United States Patent
Malek Tabrizi et al.

(10) Patent No.: US 10,792,188 B2
(45) Date of Patent: Oct. 6, 2020

(54) SYSTEMS AND METHODS FOR HIGH SPEED MODULATION OF A RESONANT SCANNER IN OPHTHALMIC LASER APPLICATIONS

(71) Applicant: AMO DEVELOPMENT, LLC, Santa Ana, CA (US)

(72) Inventors: Alireza Malek Tabrizi, Fremont, CA (US); Hong Fu, Pleasanton, CA (US); James E. Hill, Santa Ana, CA (US); Zenon Witowski, Rancho Santa Margarita, CA (US)

(73) Assignee: AMO Development, LLC, Santa Ana, CA (US)

( * ) Notice: Subject to any disclaimer, the term of this patent is extended or adjusted under 35 U.S.C. 154(b) by 364 days.

(21) Appl. No.: 15/782,791

(22) Filed: Oct. 12, 2017

(65) Prior Publication Data
US 2019/0110926 A1    Apr. 18, 2019

(51) Int. Cl.
A61F 9/008 (2006.01)
(52) U.S. Cl.
CPC ........ *A61F 9/00836* (2013.01); *A61F 9/0084* (2013.01); *A61F 9/00827* (2013.01); *A61F 2009/00848* (2013.01); *A61F 2009/00872* (2013.01); *A61F 2009/00897* (2013.01)
(58) Field of Classification Search
CPC ................ A61F 9/00836; A61F 9/0084; A61F 9/00827; A61F 2009/00848; A61F 2009/008782; A61F 2009/00897
USPC .......................................................... 606/5
See application file for complete search history.

(56) References Cited

U.S. PATENT DOCUMENTS

| | | | |
|---|---|---|---|
| 4,665,913 A | 5/1987 | L'Esperance, Jr. |
| 4,669,466 A | 6/1987 | L'Esperance |
| 4,732,148 A | 3/1988 | L'Esperance, Jr. |
| 4,764,930 A | 8/1988 | Bille et al. |
| 4,770,172 A | 9/1988 | L'Esperance, Jr. |
| 4,773,414 A | 9/1988 | L'Esperance, Jr. |
| 5,108,388 A | 4/1992 | Trokel |

(Continued)

FOREIGN PATENT DOCUMENTS

| | | |
|---|---|---|
| WO | 2016209312 A1 | 12/2016 |
| WO | 2017005815 A1 | 1/2017 |

OTHER PUBLICATIONS

International Search Report and Written Opinion for Application No. PCT/IB2018/057804, dated Jan. 21, 2019, 20 pages.

*Primary Examiner* — Aaron F Roane
(74) *Attorney, Agent, or Firm* — Johnson & Johnson Surgical Vision, Inc.

(57) ABSTRACT

An ophthalmic surgical laser system includes: a laser that produces a pulsed laser beam having a pulse energy and pulse repetition rate; a high frequency fast scanner; an XY-scan device; a Z-scan device; and a controller. The controller controls the high frequency scanner to produce a scan line having a scan width; controls the XY-scan device and the Z-scan device to carry out of first sweep of the scan line in a first sweep direction and to carry out a second sweep of the scan line in a second sweep direction that is not parallel to the first sweep direction thereby defining an overlap region. At least one of the pulse energy, repetition rate, XY-scan speed, and the scan width is varied so as to accelerate the cutting speed and reduce the exposure of ophthalmic tissue in the overlap region to multiple exposures of laser pulses configured to modify ophthalmic tissue.

11 Claims, 22 Drawing Sheets

(56) References Cited

U.S. PATENT DOCUMENTS

| | | |
|---|---|---|
| 5,163,934 A | 11/1992 | Munnerlyn |
| 5,207,668 A | 5/1993 | L'Esperance, Jr. |
| 5,219,343 A | 6/1993 | L'Esperance, Jr. |
| 5,646,791 A | 7/1997 | Glockler |
| 5,993,438 A | 11/1999 | Juhasz et al. |
| 6,315,413 B1 | 11/2001 | Shimmick et al. |
| 8,260,024 B2 | 9/2012 | Farrer et al. |
| 8,394,084 B2 | 3/2013 | Blumenkranz et al. |
| 8,403,921 B2 | 3/2013 | Blumenkranz et al. |
| 8,690,862 B2 | 4/2014 | Palanker et al. |
| 8,709,001 B2 | 4/2014 | Blumenkranz et al. |
| 9,521,949 B2 | 12/2016 | Bor et al. |
| 2011/0172649 A1 | 7/2011 | Schuele |
| 2012/0029491 A1 | 2/2012 | Rathjen et al. |

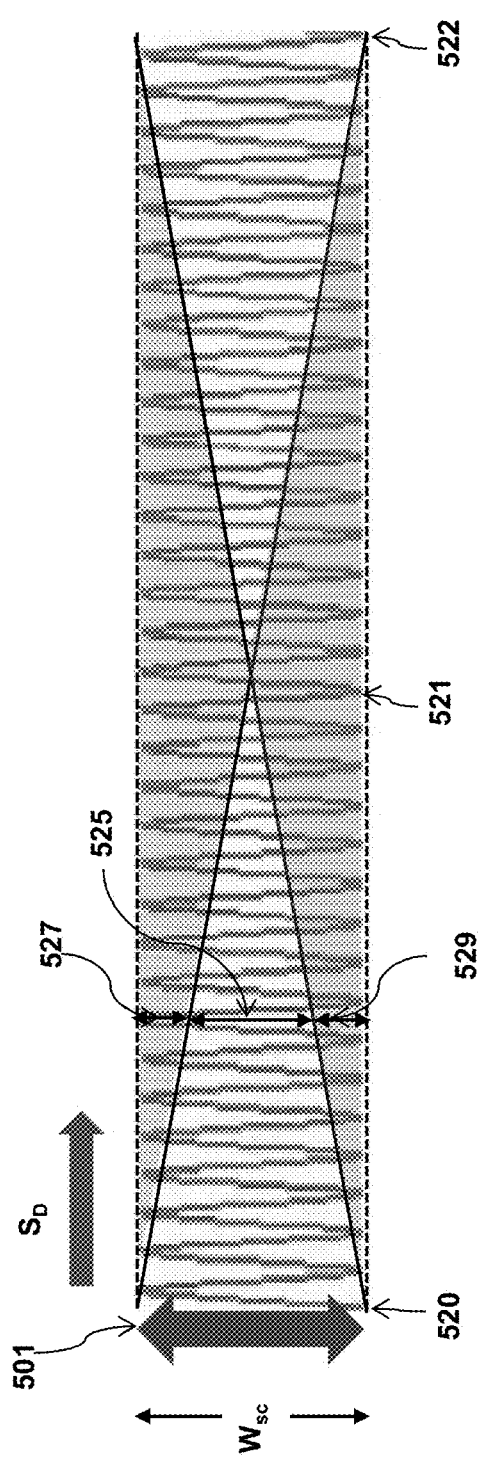
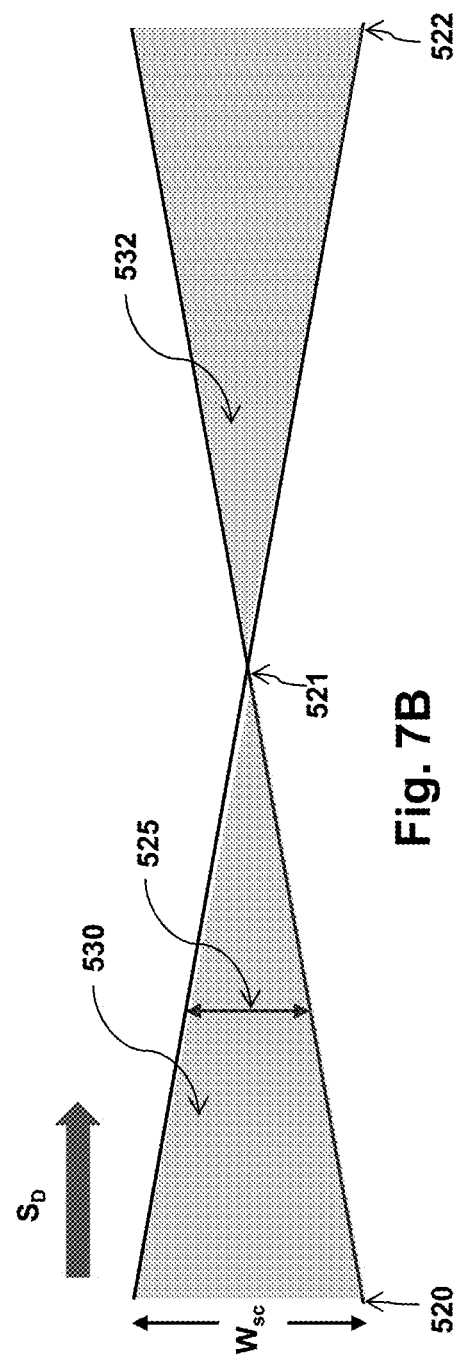
Fig. 7A
Fig. 7B

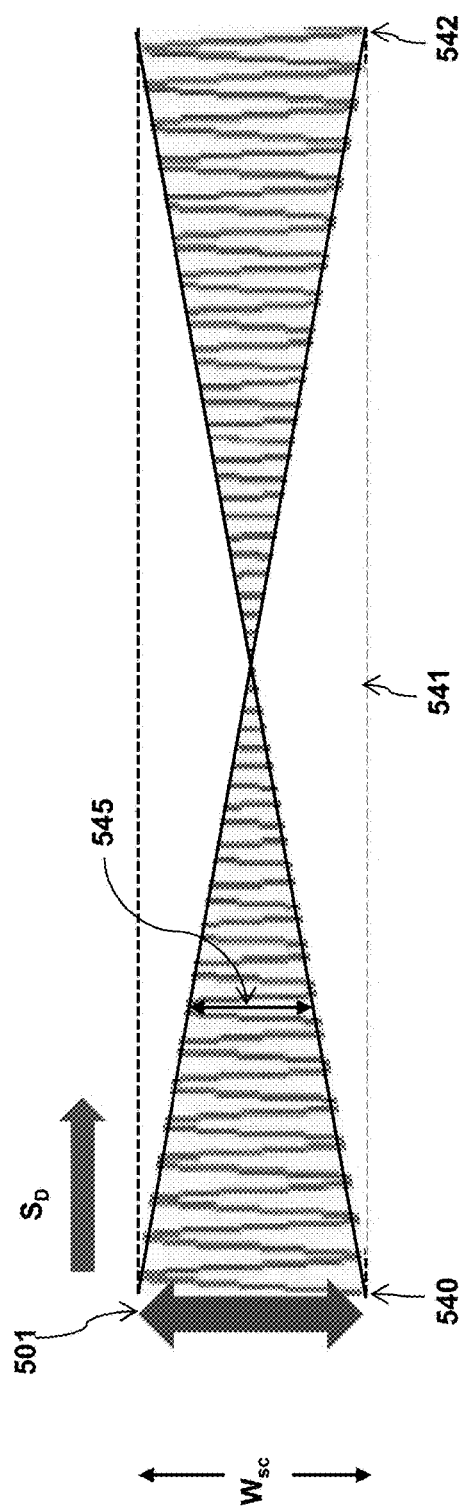
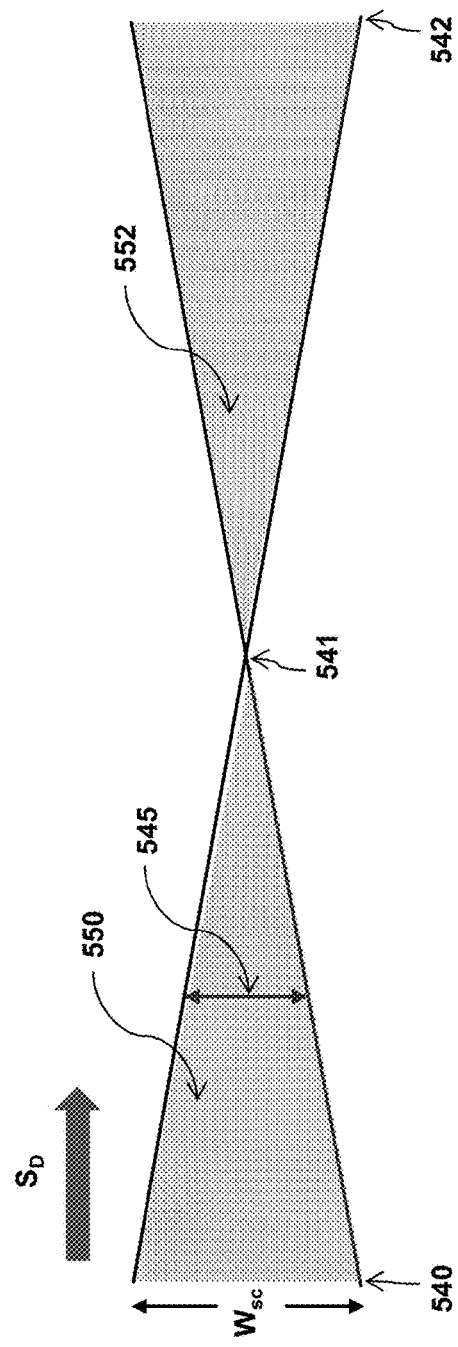
Fig. 8A
Fig. 8B

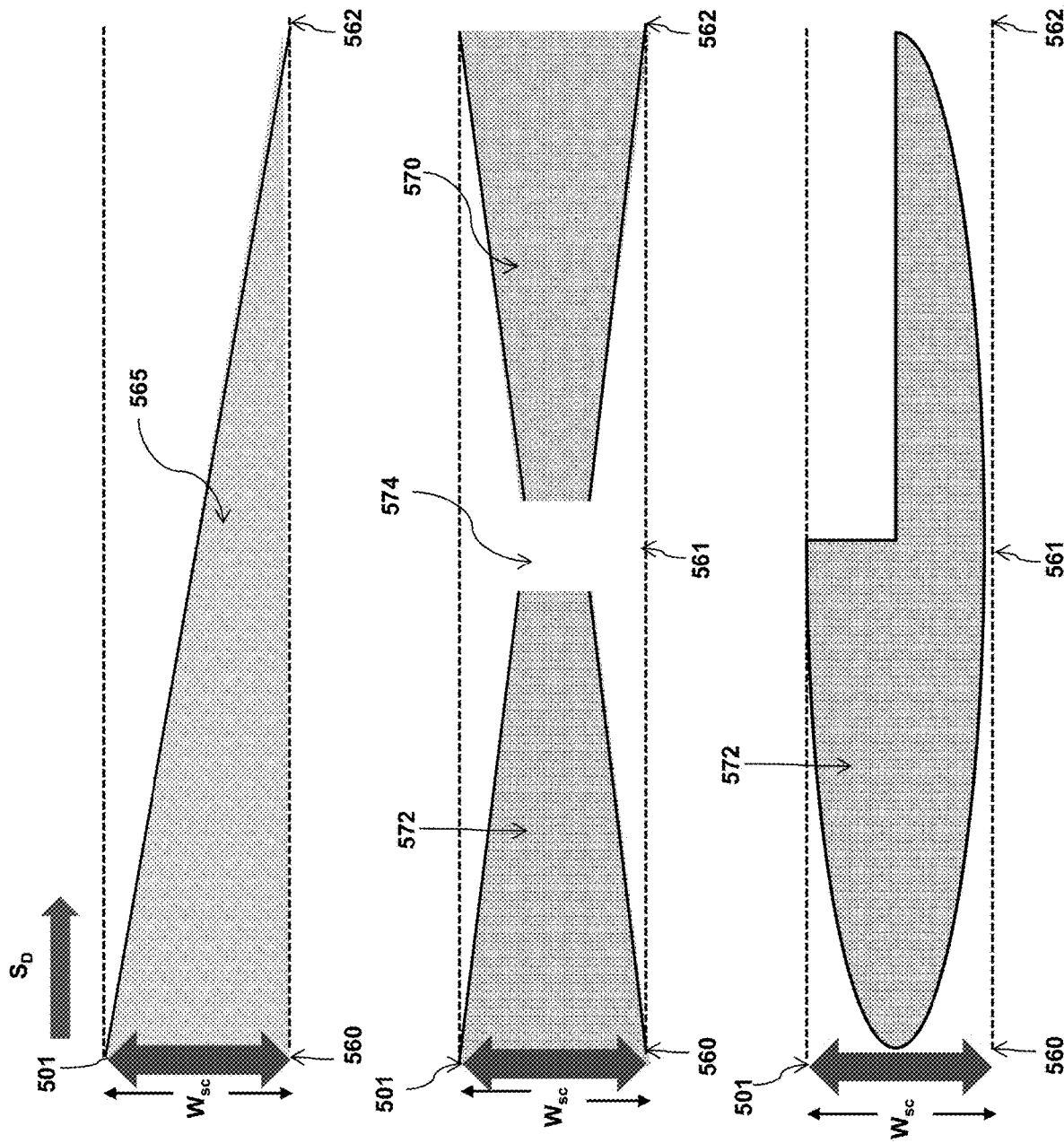

SYSTEMS AND METHODS FOR HIGH SPEED MODULATION OF A RESONANT SCANNER IN OPHTHALMIC LASER APPLICATIONS

FIELD OF THE INVENTION

Embodiments of this invention relate generally to laser-assisted ophthalmic procedures, and more particularly, to systems and methods for achieving improved ophthalmic incisions, including lenticular incisions in the cornea.

BACKGROUND OF THE INVENTION

Vision impairments such as myopia (near-sightedness), hyperopia and astigmatism can be corrected using eyeglasses or contact lenses. Alternatively, the cornea of the eye can be reshaped surgically to provide the needed optical correction. Eye surgery has become commonplace with some patients pursuing it as an elective procedure to avoid using contact lenses or glasses to correct refractive problems, and others pursuing it to correct adverse conditions such as cataracts. And, with recent developments in laser technology, laser surgery is becoming the technique of choice for ophthalmic procedures. The reason eye surgeons prefer a surgical laser beam over manual tools like microkeratomes and forceps is that the laser beam can be focused precisely on extremely small amounts of ocular tissue, thereby enhancing accuracy and reliability of the procedure. These in turn enable better wound healing and recovery following surgery.

Hyperopia (far-sightedness) is a visual impairment where light entering the eye does not focus at the retina to produce a sharp image as desired, but rather focuses at a location behind the retina such that a patient sees a blurred disc. The basic principle to treating hyperopia is to add positive focusing power to the cornea. For instance, a hyperopic eye can be treated by placing a convex lens in front of the eye to add a positive focusing power to the eye. After correction, light passing through the convex lens and into the eye focuses at the retina to form a sharp image.

Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm. Examples of laser systems that provide ultra-short pulsed laser beams include the Abbott Medical Optics iFS Advanced Femtosecond Laser, the IntraLase FS Laser, and OptiMedica's Catalys Precision Laser System.

Prior surgical approaches for reshaping the cornea include laser assisted in situ keratomileusis (hereinafter "LASIK"), photorefractive keratectomy (hereinafter "PRK") and Small Incision Lens Extraction (hereinafter "SmILE").

In the LASIK procedure, an ultra-short pulsed laser is used to cut a corneal flap to expose the corneal stroma for photoablation with ultraviolet beams from an excimer laser. Photoablation of the corneal stroma reshapes the cornea and corrects the refractive condition such as myopia, hyperopia, astigmatism, and the like.

It is known that if part of the cornea is removed, the pressure exerted on the cornea by the aqueous humor in the anterior chamber of the eye will act to close the void created in the cornea, resulting in a reshaped cornea. By properly selecting the size, shape and location of a corneal void, one can obtain the desired shape, and hence, the desired optical properties of the cornea.

In current laser surgery treatments that correct hyperopia using LASIK and PRK, positive focusing power is added to the cornea by steepening the curvature of the cornea, by for example, removing a ring-shaped stroma material from the cornea. In a LASIK procedure, a flap is first created, then lifted up for the ring-shaped stroma material to be removed or ablated away by an excimer laser. The center of the cornea is not removed while more outward portions of the cornea are removed. The flap is then put back into place. The cornea thus steepens due to the void created in the cornea. Common patterns that steepen the cornea include ring, tunnel and toric shapes. LASIK can typically correct hyperopia for up to 5 D (diopter). In a PRK procedure where no flap is created, the epithelium layer is first removed, and the ring-shaped stroma material is then removed by an excimer laser. The epithelium layer will grow back within a few days after the procedure.

Recently, surgeons have started using another surgical technique other than LASIK and PRK for refractive correction. Instead of ablating corneal tissue with an excimer laser following the creation of a corneal flap, the newer SmILE technique involves tissue removal with two femtosecond laser incisions that intersect to create a lenticule for extraction. Lenticular extractions can be performed either with or without the creation of a corneal flap. With the flapless procedure, a refractive lenticule is created in the intact portion of the anterior cornea and removed through a small incision.

In the SmILE procedure illustrated in FIG. 10, a femtolaser 110 is used to make a side cut 120, an upper surface cut 130 and a lower surface cut 140 that form a cut lens 150. A tweezer, for example, is then used to extract the cut lens beneath the anterior surface of the cornea 160 through the side cut 120. Recently, SmILE has been applied to treat myopia by cutting and extracting a convex lens-shaped stroma material with a femtosecond laser. However, SmILE techniques have not been applied in treating hyperopia.

Furthermore, as shown in FIG. 1, conventional femtosecond laser surgery systems generate a curved dissection surface to make a lenticular incision by scanning a laser focus on the intended dissection surface through a XY-scanning device and a Z-scanning device. This method does not use the more advantageous "fast-scan-slow-sweep" scanning scheme with femtosecond lasers having high repetition rate ("rep rate"), for e.g., in the MHz range. Using the "fast-scan-slow-sweep" scanning scheme for a lenticular incision, however, will generate vertical "steps" and will require many vertical side cuts, resulting in a lenticular dissection surface that is not smooth. However, as shown in FIGS. 18A and 18B, multiple sweeps of the "fast-scan-slow-sweep" scanning scheme necessary to perform certain incisions may overlap, resulting in localized high energy regions where the scans overlap. The multiple exposures of tissue modifying energy may produce unwanted tissue heating and degrade the quality of incisions.

Therefore, there is a need for improved systems and methods to generate improved ophthalmic incisions, particularly corneal lenticular incisions, for high repetition rate femtosecond lasers to correct hyperopia.

SUMMARY OF THE INVENTION

Hence, to obviate one or more problems due to limitations and disadvantages of the related art, this disclosure provides embodiments including an ophthalmic surgical laser system comprising a laser delivery system for delivering a pulsed laser beam to a target in a subject's eye, an XY-scan device to deflect the pulsed laser beam, a Z-scan device to modify a depth of a focus of the pulsed laser beam, and a controller configured to control the high frequency scanner to produce a scan line, the scan line having a scan energy and scan width; control the XY-scan device and the Z-scan device to carry out of first sweep of the scan line in a first sweep direction; control the XY-scan device and the Z-scan device to carry out a second sweep of the scan line in a second sweep direction that is not parallel to the first sweep direction, thereby defining an overlap region, wherein at least one of the pulse energy, repetition rate, XY-scan speed and the scan width are varied during at least one of the first sweep and second sweep so as to reduce the exposure of ophthalmic tissue in the overlap region to multiple exposures of laser pulses configured to modify ophthalmic tissue.

In some embodiments, the energy and/or repetition rate along the scan line is varied during a sweep sequences so that only a portion of a scan width is configured to modify ophthalmic tissue in overlap regions produced by multiple sweep sequences. By varying the energy and/or repetition rate and thus controlling the shape of the incising region during one or more sweep sequences of the target ophthalmic tissue, one can perform high quality incisions throughout an overlap region while reducing the portion of ophthalmic tissue in the overlap region to multiple exposures of high energy laser pulses configured to modify ophthalmic tissue.

In some embodiments, at least one of the pulse energy, repetition rate and/or XY-scan speed are varied such that an incising portion of the scan line varies during at least one of the first and second sweeps, thereby defining an incision region of the sweep. A shape of the incision region may further include one or more parallelograms, rectangles, pentagons, hexagons, conic sections such as parabolas and hyperbolas, circles, tear shapes, chord shapes and cross shapes.

In some embodiments, a size of the scan width $W_{sc}$ of scan line is varied along a sweep sequence in overlap regions produced by multiple sweep sequences. By size of the scan width and thus controlling the shape of the incising region during one or more sweeps of the target ophthalmic tissue, one can perform high quality incisions throughout an overlap region while reducing the portion of ophthalmic tissue in the overlap region that is subject to multiple exposures of high energy laser pulses configured to modify ophthalmic tissue.

In some embodiments, the controller may form a top lenticular incision and a bottom lenticular incision of a cornea on the subject's eye. The scan line is typically tangential to the parallels of latitude of the cornea. The scan line is then typically moved along the meridians of longitude of the cornea. The top lenticular incision is moved over the top surface through the apex of the top surface, and the bottom lenticular incision is moved over the bottom surface through the apex of bottom surface.

Other embodiments disclose an ophthalmic surgical laser system comprising a laser delivery system for delivering a pulsed laser beam to a target in a subject's eye, an XY-scan device to deflect the pulsed laser beam, a Z-scan device to modify a depth of a focus of the pulsed laser beam, and a controller configured to form a top concave lenticular incision and a bottom concave lenticular incision of a lens on the subject's eye.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

FIG. 7A illustrates and exemplary scanning of the surgical ophthalmic laser system according to the present invention in which an energy of a portion of the scan line is varied along a sweep direction according to an embodiment of the present invention.

FIG. 7B illustrates a shape of the tissue modification regions produced according to the embodiment of FIG. 7A.

FIG. 8A illustrates and exemplary scanning of the surgical ophthalmic laser system according to the present invention in which a width the scan line is varied along a sweep direction according to an embodiment of the present invention.

FIG. 8B illustrates a shape of the tissue modification regions produced according to the embodiment of FIG. 8A.

FIGS. 9A, 9B and 9C illustrate exemplary other shapes of tissue modification regions produced by scanning of the surgical ophthalmic laser system according to the present invention according to other embodiments of the present invention.

DETAILED DESCRIPTION OF THE PREFERRED EMBODIMENTS

Embodiments of this invention are generally directed to systems and methods for laser-assisted ophthalmic procedures, and more particularly, to systems and methods for lenticular laser incisions.

Figure 1:
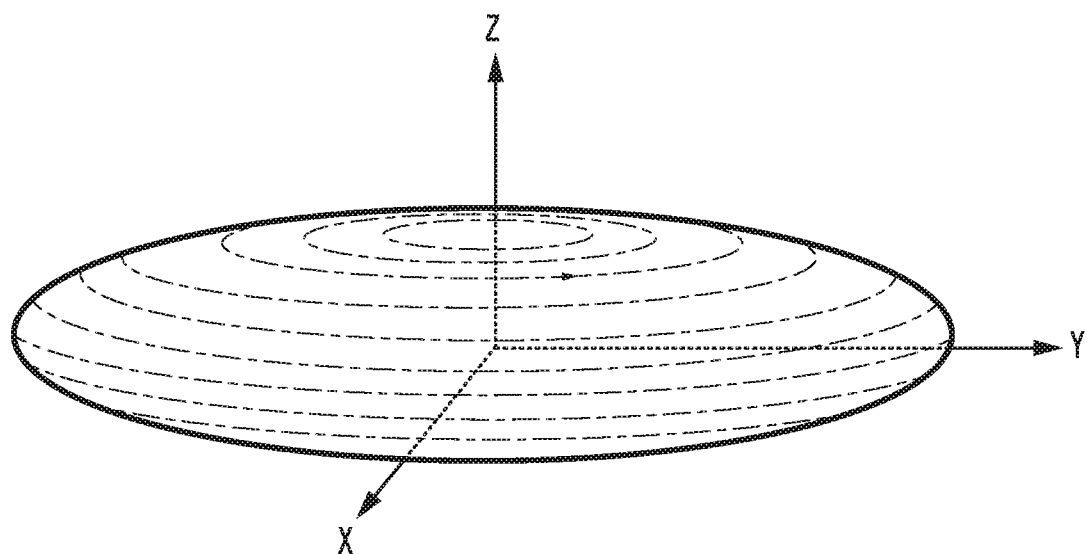
FIG. 1 illustrates a conventional lenticular cut via scanning a single focus spot.
Figure 2:
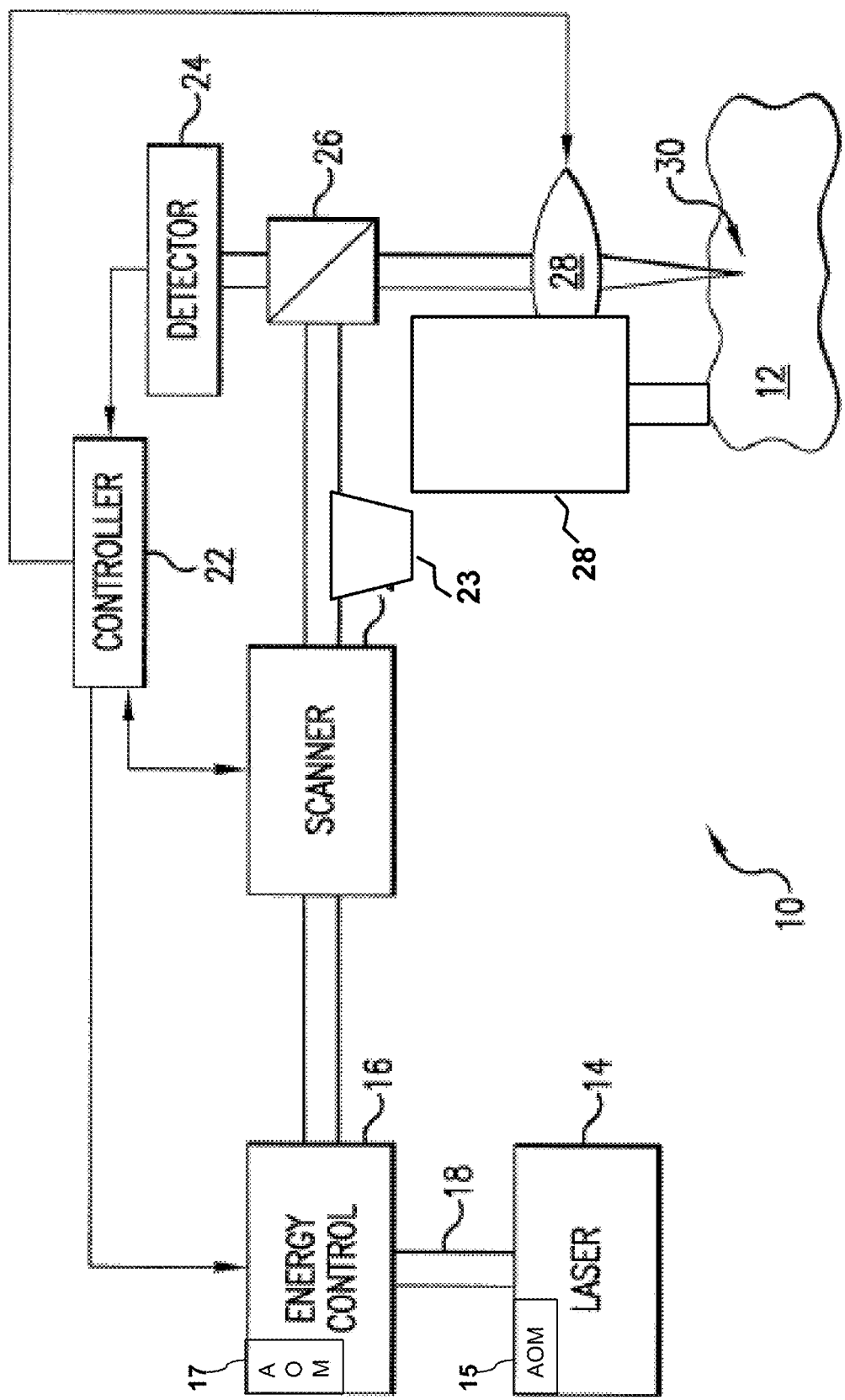
FIG. 2 is a simplified diagram of a surgical ophthalmic laser system according to an embodiment of the present invention.

Referring to the drawings, FIG. 2 shows a system 10 for making an incision in a material 12. The system 10 includes, but is not limited to, a laser 14 capable of generating a pulsed laser beam 18, an energy control module 16 for varying the pulse energy of the pulsed laser beam 18, a Z-scanner 20 for modifying the depth of the pulse laser beam 18, a controller 22, a prism 23 (e.g., a Dove or Pechan prism, or the like), and an XY-scanner 28 for deflecting or directing the pulsed laser beam 18 from the laser 14 on or within the material 12.

The controller 22, such as a processor operating suitable control software, is operatively coupled with the Z-scanner 20, the XY-scanner 28, and the energy control unit 16 to direct a scan line 30 of the pulsed laser beam along a scan pattern on or in the material 12. In this embodiment, the system 10 further includes a beam splitter 26 and a detector 24 coupled to the controller 22 for a feedback control mechanism (not shown) of the pulsed laser beam 18. Other feedback methods may also be used, including but not necessarily limited to position encoder on the scanner 20, or the like. In an embodiment, the pattern of pulses may be summarized in machine readable data of tangible storage media in the form of a treatment table. The treatment table may be adjusted according to feedback input into the controller 22 from an automated image analysis system in response to feedback data provided from an ablation monitoring system feedback system (not shown). Optionally, the feedback may be manually entered into the controller 22 by a system operator. The feedback may also be provided by integrating a wavefront measurement system (not shown) with the laser surgery system 10. The controller 22 may continue and/or terminate a sculpting or incision in response to the feedback, and may also modify the planned sculpting or incision based at least in part on the feedback. Measurement and imaging systems are further described in U.S. Pat. Nos. 6,315,413 and 8,260,024, the complete disclosures of which are incorporated herein by reference.

In an embodiment, the system 10 uses a pair of scanning mirrors or other optics (not shown) to angularly deflect and scan the pulsed laser beam 18. For example, scanning mirrors driven by galvanometers may be employed where each of the mirrors scans the pulsed laser beam 18 along one of two orthogonal axes. A focusing objective (not shown), whether one lens or several lenses, images the pulsed laser beam 18 onto a focal plane of the system 10. The focal point of the pulsed laser beam 18 may thus be scanned in two dimensions (e.g., the x-axis and the y-axis) within the focal plane of the system 10. Scanning along the third dimension, i.e., moving the focal plane along an optical axis (e.g., the z-axis), may be achieved by moving the focusing objective, or one or more lenses within the focusing objective, along the optical axis.

Laser 14 may comprise a femtosecond laser capable of providing pulsed laser beams, which may be used in optical procedures, such as localized photodisruption (e.g., laser induced optical breakdown). Localized photodisruptions can be placed at or below the surface of the material to produce high-precision material processing. For example, a micro-optics scanning system may be used to scan the pulsed laser beam to produce an incision in the material, create a flap of the material, create a pocket within the material, form removable structures of the material, and the like. The term "scan" or "scanning" refers to the movement of the focal point of the pulsed laser beam along a desired path or in a desired pattern.

In other embodiments, the laser 14 may comprise a laser source configured to deliver an ultraviolet laser beam comprising a plurality of ultraviolet laser pulses capable of photodecomposing one or more intraocular targets within the eye.

Laser 14 typically comprises an acousto-optic module 15 for controlling the energy and/or repetition rate of the laser pulses. As described herein acousto-optic module 15 of the laser 14 may optionally be used control one or more of the pulse energy, repetition rate and scan width of a scan line in accordance with many embodiments of the present invention.

Energy control unit 16 may optionally comprise a second acousto-optic module 17 for controlling the energy and/or repetition rate of the laser pulses. As described herein acousto-optic module 15 of the laser 14 may optionally be used control one or more of the pulse energy, repetition rate and scan width of a scan line in accordance with many embodiments of the present invention.

Although the laser system 10 may be used to photoalter a variety of materials (e.g., organic, inorganic, or a combination thereof), the laser system 10 is suitable for ophthalmic applications in some embodiments. In these cases, the focusing optics direct the pulsed laser beam 18 toward an eye (for example, onto or into a cornea) for plasma mediated (for example, non-UV) photoablation of superficial tissue, or into the stroma of the cornea for intrastromal photodisruption of tissue. In these embodiments, the surgical laser system 10 may also include a lens to change the shape (for example, flatten or curve) of the cornea prior to scanning the pulsed laser beam 18 toward the eye.

The laser system 10 is capable of generating the pulsed laser beam 18 with physical characteristics similar to those of the laser beams generated by a laser system disclosed in U.S. Pat. Nos. 4,764,930, 5,993,438, and U.S. patent application Ser. No. 12/987,069, filed Jan. 7, 2011, which are incorporated herein by reference.

Figure 3:
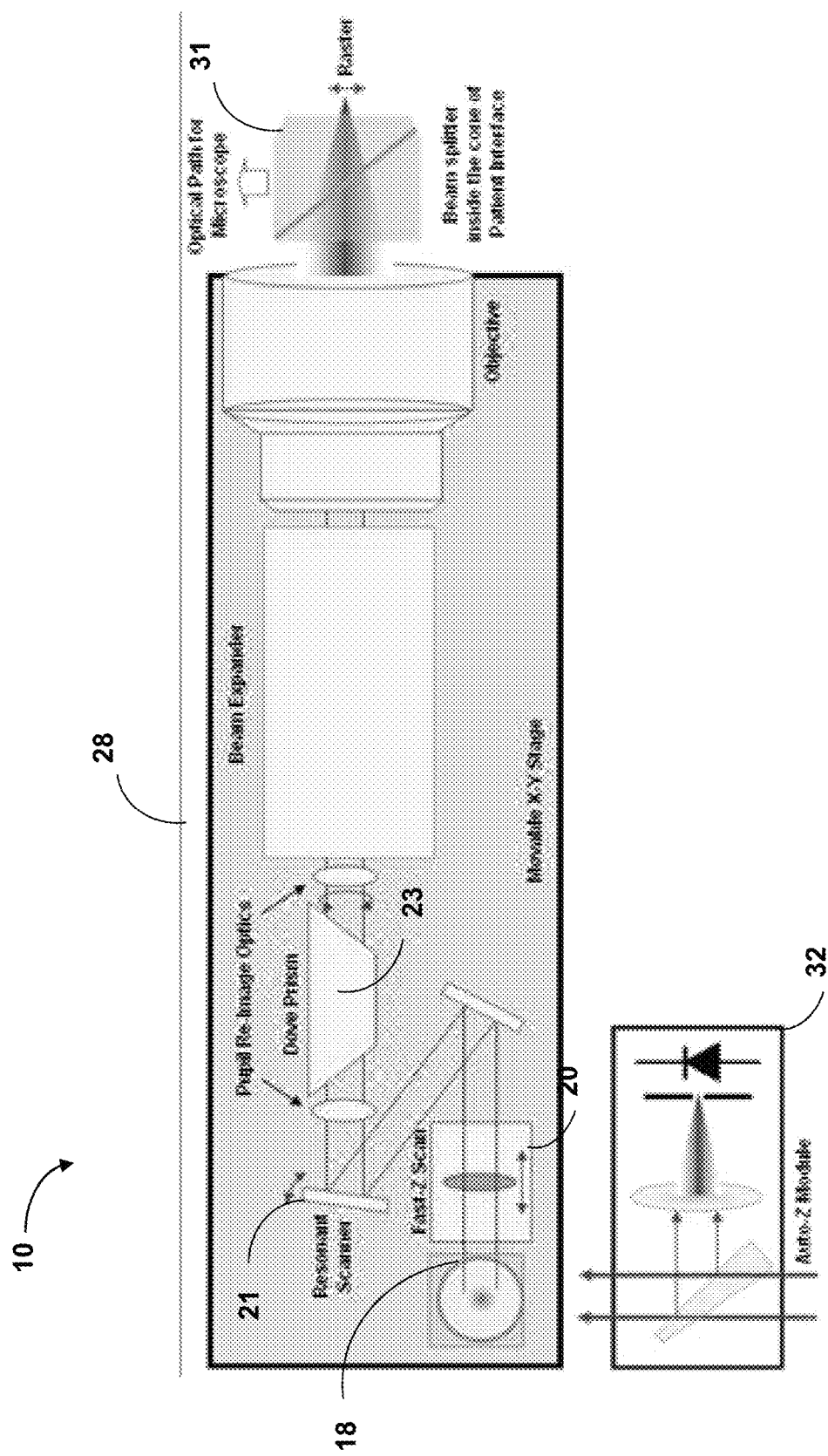
FIG. 3 is another simplified diagram of a surgical ophthalmic laser system according to an embodiment of the present invention.

FIG. 3 shows another exemplary diagram of the laser system 10. FIG. 3 shows a moveable XY-scanner (or XY-stage) 28 of a miniaturized femtosecond laser system. In this embodiment, the system 10 uses a femtosecond oscillator, or a fiber oscillator-based low energy laser. This allows the laser to be made much smaller. The laser-tissue interaction is in the low-density-plasma mode. An exemplary set of laser parameters for such lasers include pulse energy in the 50-100 nJ range and pulse repetitive rates (or "rep rates") in the 5-20 MHz range. A fast-Z scanner 20 and a resonant scanner 21 direct the laser beam 18 to the prism 23. When used in an ophthalmic procedure, the system 10 also includes a patient interface 31 design that has a fixed cone nose and a portion that engages with the patient's eye. A beam splitter is placed inside the cone of the patient interface to allow the whole eye to be imaged via visualization optics. In one embodiment, the system 10 uses: optics with a high numerical aperture (NA) of about 0.3-0.8, which would produce less than 3 µm Full Width at Half Maximum (FWHM) focus spot size; and a resonant scanner 21 that produces 1-2 mm scan line (i.e. a line raster pattern with a scan width $W_{sc}$ of about 1-2 mm) with the XY-scanner scanning the resonant scan line to a 10 mm field. And, in a preferred embodiment, the system 10 uses optics of about 0.6 NA, which would produce about 1.1 µm Full Width at Half Maximum (FWHM) focus spot size. The prism 23 rotates the resonant scan line in any direction on the XY plane. The fast-Z scanner 20 sets the incision depth and produces a side cut. The system 10 may also include an auto-Z module 32 to provide depth reference. The miniaturized femtosecond laser system 10 may be a desktop system so that the patient sits upright while being under treatment. This eliminates the need of certain opto-mechanical arm mechanism(s), and greatly reduces the complexity, size, and weight of the laser system. Alternatively, the miniaturized laser system may be designed as a conventional femtosecond laser system, where the patient is treated while lying down.

Figure 4:
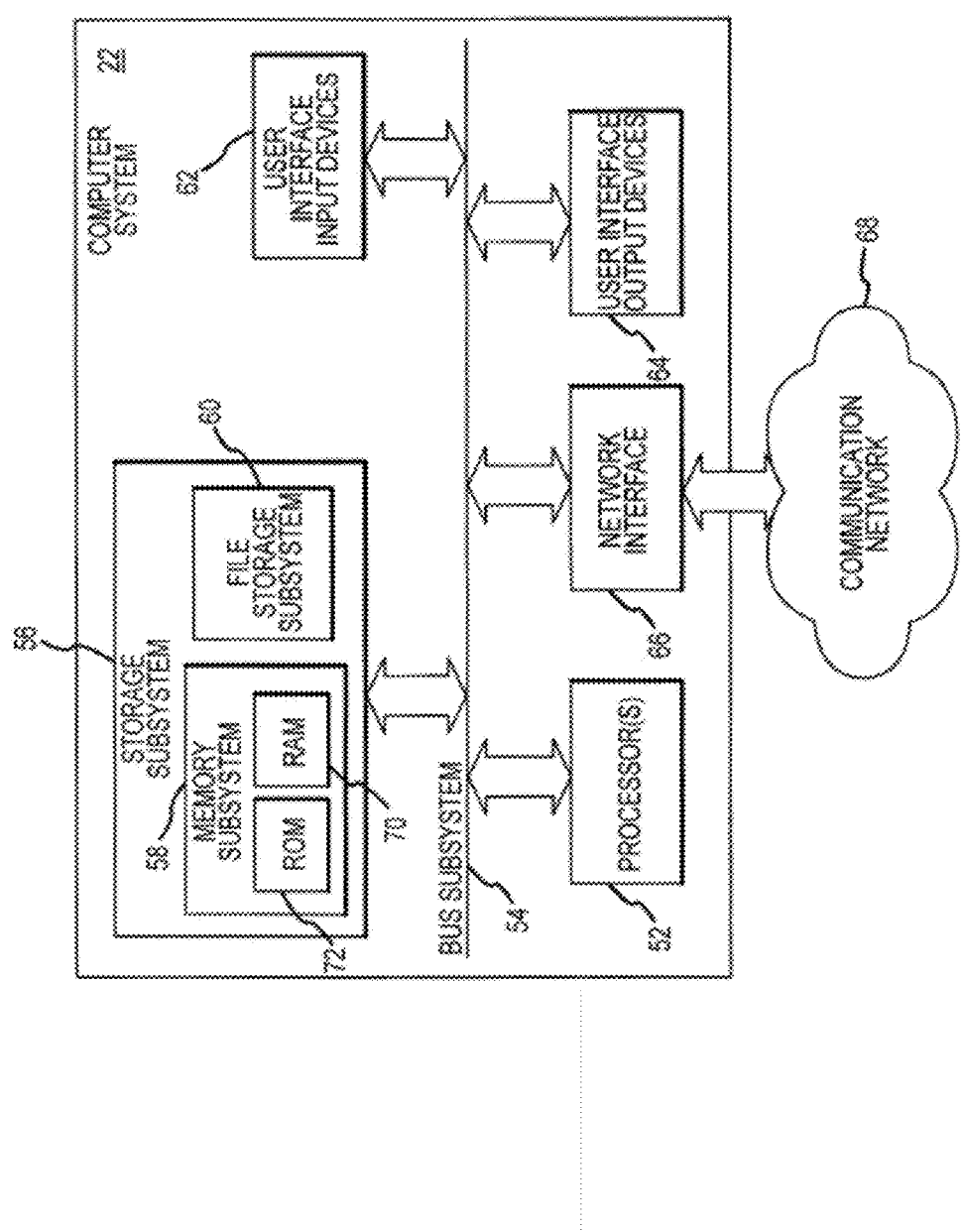
FIG. 4 is a simplified diagram of a controller of a surgical ophthalmic laser system according to an embodiment of the present invention.

FIG. 4 illustrates a simplified block diagram of an exemplary controller 22 that may be used by the laser system 10 according to an embodiment of this invention. Controller 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices. Network interface subsystem 66 includes one or more interfaces known in the arts, such as LAN, WLAN, Bluetooth, other wire and wireless interfaces, and so on.

User interface input devices 62 may include a keyboard, pointing devices such as a mouse, trackball, touch pad, or graphics tablet, a scanner, foot pedals, a joystick, a touch screen incorporated into a display, audio input devices such as voice recognition systems, microphones, and other types of input devices. In general, the term "input device" is intended to include a variety of conventional and proprietary devices and ways to input information into controller 22.

User interface output devices 64 may include a display subsystem, a printer, a fax machine, or non-visual displays such as audio output devices. The display subsystem may be a flat-panel device such as a liquid crystal display (LCD), a light emitting diode (LED) display, a touchscreen display, or the like. The display subsystem may also provide a non-visual display such as via audio output devices. In general, the term "output device" is intended to include a variety of conventional and proprietary devices and ways to output information from controller 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files. File storage subsystem 60 may include a hard disk drive along with associated removable media, a Compact Disk (CD) drive, an optical drive, DVD, solid-state memory, and/or other removable media. One or more of the drives may be located at remote locations on other connected computers at other sites coupled to controller 22. The modules implementing the functionality of the present invention may be stored by file storage subsystem 60.

Bus subsystem 54 provides a mechanism for letting the various components and subsystems of controller 22 communicate with each other as intended. The various subsystems and components of controller 22 need not be at the same physical location but may be distributed at various locations within a distributed network. Although bus subsystem 54 is shown schematically as a single bus, alternate embodiments of the bus subsystem may utilize multiple busses.

Due to the ever-changing nature of computers and networks, the description of controller 22 depicted in FIG. 4 is intended only as an example for purposes of illustrating only one embodiment of the present invention. Many other configurations of controller 22, having more or fewer components than those depicted in FIG. 4, are possible.

As should be understood by those of skill in the art, additional components and subsystems may be included with laser system 10. For example, spatial and/or temporal integrators may be included to control the distribution of energy within the laser beam, as described in U.S. Pat. No. 5,646,791, which is incorporated herein by reference. Ablation effluent evacuators/filters, aspirators, and other ancillary components of the surgical laser system are known in the art, and may be included in the system. In addition, an imaging device or system may be used to guide the laser beam. Further details of suitable components of subsystems that can be incorporated into an ophthalmic laser system for performing the procedures described here can be found in commonly-assigned U.S. Pat. Nos. 4,665,913, 4,669,466, 4,732,148, 4,770,172, 4,773,414, 5,207,668, 5,108,388, 5,219,343, 5,646,791, 5,163,934, 8,394,084, 8,403,921, 8,690,862, 8,709,001, U.S. application Ser. No. 12/987,069, filed Jan. 7, 2011, and U.S. application Ser. No. 13/798,457 filed Mar. 13, 2013, which are incorporated herein by reference.

In an embodiment, the laser surgery system 10 includes a femtosecond oscillator-based laser operating in the MHz range, for example, 10 MHz, for example, from several MHz to tens of MHz. For ophthalmic applications, the XY-scanner 28 may utilize a pair of scanning mirrors or other optics (not shown) to angularly deflect and scan the pulsed laser beam 18. For example, scanning mirrors driven by galvanometers may be employed, each scanning the pulsed laser beam 18 along one of two orthogonal axes. A focusing objective (not shown), whether one lens or several lenses, images the pulsed laser beam onto a focal plane of the laser surgery system 10. The focal point of the pulsed laser beam 18 may thus be scanned in two dimensions (e.g., the X-axis and the Y-axis) within the focal plane of the laser surgery system 10. Scanning along a third dimension, i.e., moving the focal plane along an optical axis (e.g., the Z-axis), may be achieved by moving the focusing objective, or one or more lenses within the focusing objective, along the optical axis. It is noted that in many embodiments, the XY-scanner 28 deflects the pulse laser beam 18 to form a scan line.

Figure 5:
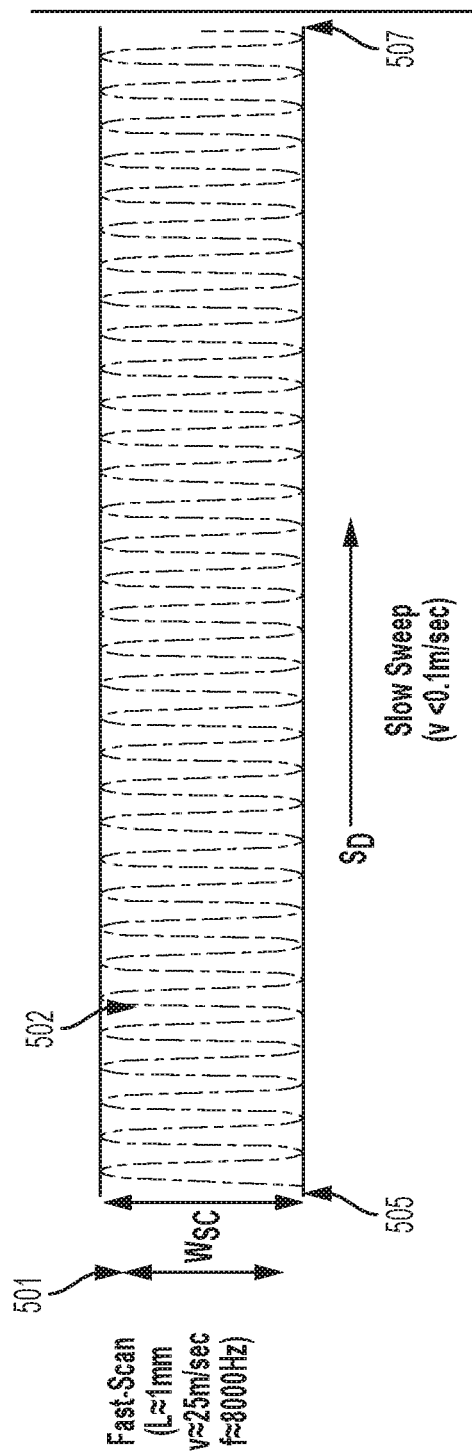
FIG. 5 illustrates an exemplary scanning of a surgical ophthalmic laser system according to an embodiment of the present invention.

In other embodiments, the beam scanning can be realized with a "fast-scan-slow-sweep" scanning scheme. The scheme consists of two scanning mechanisms: first, a high frequency fast scanner is used to produce a short, fast scan line (e.g., a resonant scanner 21 of FIG. 3); second, the fast scan line is slowly swept by much slower X, Y, and Z scan mechanisms. FIG. 5 illustrates a scanning example of a laser system 10 using an 8 kHz resonant scanner 21 to produce a scan line 501 having a scan width $W_{sc}$ of about 1 mm and a scan speed of about 25 m/sec, and X, Y, and Z scan mechanisms with the scan speed smaller than 0.1 m/sec. The fast scan line may be perpendicular to the optical beam propagation direction, i.e., it is preferably parallel to the XY plane. The trajectory $S_D$ of the slow sweep (which may be referred to herein as the scan direction $S_D$ of the slow sweep) can be any three dimensional curve drawn by the X, Y, and Z scanning devices (e.g., XY-scanner 28 and Z-scanner 20). An advantage of the "fast-scan-slow-sweep" scanning scheme is that it only uses small field optics (e.g., a field diameter of 1.5 mm) which can achieve high focus quality at relatively low cost. The large surgical field (e.g., a field diameter of 10 mm or greater) is achieved with the XY-scanner, which may be unlimited. The scanning provided by the scan line 501 as it moves along the sweep direction $S_D$ from start point 505 of the sweep to the end point 507 of the sweep is characterized by a sinusoidal curve 502. The XY stage 28 may move the scan line across a surgical field in a raster scan line scanning pattern. Raster line scanning patterns may be provided in a number of configurations and may move the scan line 501 in a sweep trajectory $S_D$ systematically across the surgical field to provide for forming all or part of the predetermined incision in a continuous slow sweep.

A plurality of incision patterns can be performed using the "fast scan slow sweep" methodology, including an xy lamellar dissection, a spiral lamellar dissection, a vertical side-cut, a plano-vertical side cut, an intrastromal incision, a lenticular incision, as well as any three-dimensional dissection. Other cuts include a flap cut for LASIK, lens cut for myopia correction, ring resection for inlay, arcuate incision for astigmatism, clear cornea incision for a cataract entry cut, penetrating cut for cornea transplant, anterior and posterior deep lamellar cut for cornea transplant, corneal ring cut for insertion of stiffening material, pocket cut to treat presbyopia, Intralase enabled keratoplasty (IEK) for corneal transplants, and so forth.

Figure 6:
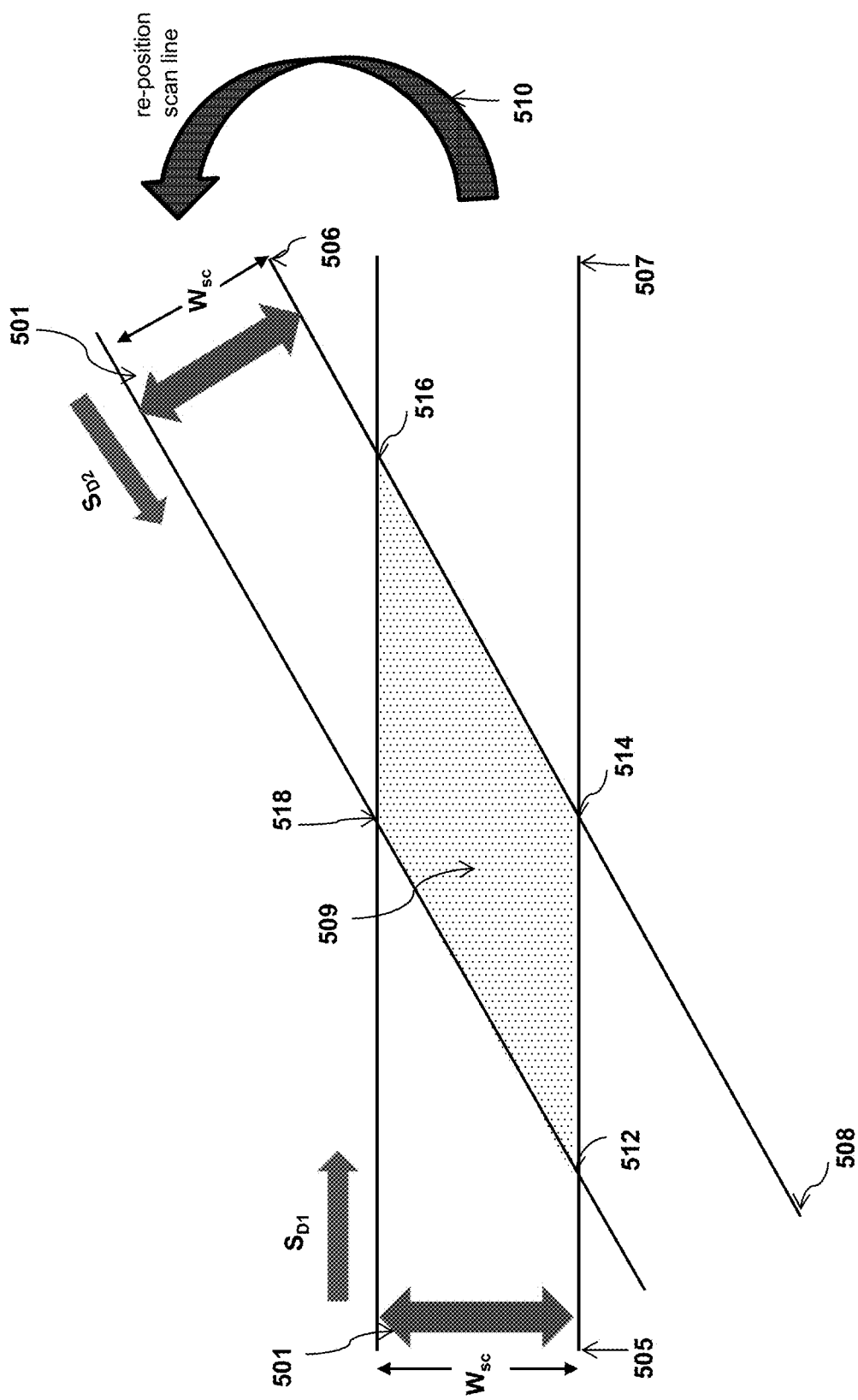
FIG. 6 illustrates an exemplary scanning of a surgical ophthalmic laser system according having two non-parallel sweeps and an overlapping region according to an embodiment of the present invention.

FIG. 6 illustrates a portion of an incision pattern characterized by overlapping cuts in which tissue is exposed multiple times to laser pulses having energy above the tissue modification thresholds. Multiple exposures result from either separate sweeps or by different portions of a raster line scanning pattern. Multiple exposures caused by crossing point of multiple sweeps across the same target ophthalmic tissue result in higher energy exposure and can cause localized excess heating and can degrade incision quality.

In FIG. 6, the XY stage and Z Stage move scan line 501 having scan width $W_{sc}$ so as to carry out a first sweep of a target ophthalmic from a first start point 505 to a first end point 507 along a first sweep trajectory $S_{D1}$. The sweep trajectory may alternatively be referred to as a sweep sequence or merely a "sweep." Subsequently, the scan line 501 is repositioned 510 by the laser optical system, and the XY stage and Z stage then move scan line 501 so as to carry out a second sweep of the target ophthalmic tissue from a second start point 506 to a second end point 508 along a second sweep trajectory $S_{D2}$ that is not parallel to the first sweep trajectory $S_{D1}$. As shown in FIG. 6, the non-parallel sweeps result in overlap region 509 defined by the crossing points 512, 514, 516, 518 of the first sweep and the second sweep. It should be noted that the first sweep and the second sweep may be different portions of a raster scan of the target ophthalmic tissue. Further, while the scan width is shown in FIG. 6 to be the same in the first sweep and the second sweep, in other embodiments, the scan width of the second sweep may be different from the scan width of the first sweep. In accordance with the present invention, at least one of the pulse energy, repetition rate and the scan width Wsc of scan line 501 are varied during at least one of the first sweep and second sweep so as to reduce an amount of ophthalmic tissue in the overlap region subject to multiple exposures of laser pulses configured to modify ophthalmic tissue. That is, at least one of the pulse energy, repetition rate and the scan width Wsc of scan line 501 are varied during at least one of the first sweep and second sweep so as that a portion of the ophthalmic tissue in the overlap region 509 is not subject to exposure to laser pulses configured to modify ophthalmic tissue in both the first and second sweep.

In some embodiments, the portion of the overlap region 509 not subject to multiple exposures is 100% of the overlap region 509. In some embodiments, the portion of the overlap region 509 not subject to multiple exposures is 95%, or 90% or 80% or 50% or 25% of the overlap region 509.

It should be noted that multiple subsequent additional sweeps of the scan line 501 of the target ophthalmic tissue may overlap with the first and second sweeps in the overlap region 509 such that a portion of overlap region 509 would be subject to 3 or more (or 4, 5, 6 or more) exposures to laser pulses configured to modify ophthalmic tissue. In such situations, at least one of the repetition rate and the scan width Wsc of scan line 501 during the sweeps are preferably varied so as to reduce an amount of ophthalmic tissue in the overlap region 509 subject to 3 or more (or 4, 5, 6 or more) exposures to laser pulses configured to modify ophthalmic tissue.

FIGS. 7A and 7B illustrate an embodiment in which the energy and/or repetition rate of the scan line 501 is varied along a sweep trajectory $S_D$ so that only a portion of the scan width is configured to modify ophthalmic tissue. As shown in FIG. 7A, a scan line 501 having a scan width $W_{sc}$ is swept in a scan trajectory $S_D$ from a start point 520 (or alternatively, a first point in a raster scan) to an end point 522 (or alternatively, a second point in a raster scan). During at least a portion the sweep, a higher energy portion 525 of the scan line is configured to modify ophthalmic tissue (which may be referred to herein as incising portion 525) and lower energy portions 527, 529 are not configured to modify ophthalmic tissues (which may be referred to herein as the non-incising portions 527, 529). In the embodiment of FIG. 7A, the size of the incising portion 525 decreases continuously as the scan line is swept along the scan trajectory and reaches a minimum at a predetermined location 521. After reaching predetermined location 521, the size of incising portion 525 continuously increases as scan line 501 is swept to end point 522. In many embodiments, the incising portion 525 of scan line 501 is comprised of laser pulses having a pulse energy and repetition rate sufficient to modify ophthalmic tissue. The non-incising portions 527, 529 are characterized by a pulse energy and/or repetition rate below the level required to modify tissue. The non-incising portions 527, 529 are generally disposed within overlap regions defined by multiple sweeps of scan line 501 over the target ophthalmic tissue.

In an alternative embodiment of FIG. 7A, the energy of the non-incising portion is reduced to zero by preferably blocking the non-incising portions 527, 529 of scan line 501 such that the non-incising portion of scan line is not incident upon the target ophthalmic tissue while permitting the incising portion 525 to continue to be directed to the target ophthalmic tissue.

By varying the size of the incising portion 525 of scan line 501 as described above, tissue incising regions 530, 532 of predetermined shape shown in FIG. 7b can be produced in an overlap region of multiple scans while portions of the overlap region outside the incising regions 530, 532 are subjected to lower energy portions of the scan line 501, or alternatively, the portions of the scan line outside the incision region is blocked. In the embodiment of FIGS. 7A and 7B, incising regions 530, 532 have a triangular shape with a vertexes touching at the predetermined minimum 512. While the embodiment of FIGS. 7A and 7B, any number of triangles could be formed during the sweep. Thus, in many embodiments, the size of the incising portion 525 may be controlled during a sweep trajectory to produce one or more triangles depending upon the application selected.

By controlling the shape of the incising region(s) as shown in FIGS. 7A and 7B during one or more sweeps of the target ophthalmic tissue, one can perform high quality incisions throughout an overlap region while reducing the portion of ophthalmic tissue in the overlap region to multiple exposures of high energy laser pulses configured to modify ophthalmic tissue.

The manner in which the pulse energy or repetition rate is varied is not particularly limited. For instance, at least one of acousto-optic modules 15, 17 can be used to control the repetition rate of the laser pulses such that a first repetition rate sufficient to modify ophthalmic tissue is used for the incising portion 525 but a second repetition rate that is not sufficient to modify ophthalmic tissue is used for the non-incising portions 527, 529. For instance, in one embodiment, the fundamental frequency of the laser 14 is 60 MHz. In an exemplary embodiment, when the AOM 15 is adjusted to pick one pulse for every 6 pulses, a pulse repetition rate of 10 MHz is achieved, which is sufficient to modify ophthalmic tissue. However, when the AOM 15 is adjusted to pick 2, 3, 4, 5, or 6 pulses for every 6 pulses, a pulse repetition rate of 20 MHz, 30 MHz, 40 MHz, 50 MHz or 60 MHz, respectively is achieved. Pulse repetitions rates above 20 MHz insufficient to modify ophthalmic tissue. Thus, in some embodiments of the present invention, the first repetition rate for the incising portion 525 is optionally 10 MHz and lower, and a second repetition rate for the non-incising portions 527, 529 is 20 MHz (or 30 MHz, 40 MHz, 50 MHz or 60 MHz) and higher. One advantage of the varying the repetition rate as described herein is that the laser remains "on" during and also maintains a uniform power throughout the sweep.

Alternatively, as would be understood by those ordinarily skilled, AOMs 15, 17 can operate as a very fast shutter to block non-incising portions 525, 527 from proceeding along the optical path. As a result, non-incising portions 525, 527 are not incident upon the target ophthalmic tissue. Conversely, incising portion 525 is not blocked and is directed along the optical path to the target ophthalmic tissue. In many embodiments, it will be preferable to use AOM 17 for blocking non-incising portion. Use of AOM 15 for this purpose may result in laser pulses with highly energy distributions.

In another embodiment, the energy of the scan line in the non-incising portions 525, 527 may be reduced to zero by turning off laser 14.

FIGS. 8A and 8B illustrate an embodiment in which only the size of the scan width $W_{sc}$ of scan line 501 is varied along a sweep trajectory. As shown in FIG. 8A, a scan line 501 having an initial scan width $W_{sc}$ is swept in a scan trajectory $S_D$ from a start point 540 (or alternatively, a first point in a raster scan) to an end point 542 (or alternatively a second point in a raster scan). During at least a portion the sweep, a size 545 of scan width is made smaller relative to the initial scan width $W_{sc}$ to modify ophthalmic tissue at the reduced size 545 as the scan line 501 is swept along scan trajectory $S_D$. In the embodiment of FIG. 8A, the size 545 of the scan line 501 decreases continuously relative to the initial size $W_{sc}$ as the scan line is swept along the scan trajectory and reaches a minimum at a predetermined location 541. At the predetermined location 541 in the minim in FIG. 8A, the size 541 of scan line 501 may be at or near zero. After reaching predetermined location 541, the size 545 of scan line 501 continuously increases as scan line 501 is swept to end point 542. In the embodiment of FIG. 8A, the scan line 501 is preferably comprised of laser pulses having a pulse energy and repetition rate sufficient to modify ophthalmic tissue during the entirety of the scan trajectory at the positions where the size 545 is non-zero.

By varying the size 525 of scan line 501, tissue incising regions 550, 552 of predetermined shape shown in FIG. 7b can be produced in an overlap region of multiple scans while portions of the overlap region outside the incising regions 550, 552 are not subjected to any tissue modifying laser pulses. In the embodiment of FIGS. 8A and 8B, tissue incising regions have a triangular shape with a vertexes touching at the predetermined minimum.

By controlling the shape of the incising region(s) as shown in FIGS. 8A and 8B during one or more sweeps of the target ophthalmic tissue, one can perform high quality incisions throughout an overlap region while reducing the portion of ophthalmic tissue in the overlap region that is subject to multiple exposures of high energy laser pulses configured to modify ophthalmic tissue.

Exemplary resonant scanners of the present invention typically include a mirror attached to a metal rod that vibrates at an inherent resonant frequency. The shape and composition of the rod are selected to operate at a desired frequency to scan laser pulses. The resonant scanner does not require a plurality of mirrors or a set of cumbersome galvos to scan across a surgical field as other systems do. Instead, the scan line may be rotated by a scan line rotator within an optical field and the scanner may be scanned across a surgical field by a moveable XY stage. The scan width Wsc of the scan line may be controlled by changing a phase of the amount of the voltage applied to the resonant scanner such that the amplitude of the modulation of the resonant scanner changes, i.e. the scan width Wsc can be modulated such that it becomes larger or smaller.

It should be noted that decreasing the scan width as described in the embodiment of FIGS. 8A and 8B may have the effect of substantially changing the energy density of the laser line scan 501 as the scan width is decreased during the sweep sequence. This is because the laser pulses of the scan line move more slowly at the turnaround of the scan line and as such, the laser pulses of the scan line are more closely spaced at or near turnarounds in the scan line. As such, another aspect of this embodiment typically includes adjusting the energy density during the scan sequence so that the energy density is maintained substantially constant as the size of the scan width is changed. This is done so that the energy density in the incised portions does is substantially the same throughout the sweep sequence.

The shape of the incising region(s) obtained by varying at least one of the pulse energy, repetition rate and scan width in an overlap region during a sweep of the scan line is not particularly limited. Exemplary features of different embodiments of the incision regions are shown in FIGS. 9A, 9B and 9C. FIG. 9A shows an incision region 565 that is triangle shaped, specifically a right triangle, in which a size of the incising region decreases as the scan line 501 is swept in a sweep trajectory SD from a first point 560 to a second point 562. FIG. 9B shows trapezoid shaped incision regions 570, 572 with a discontinuous region 574 at or near a predetermined region 561 of the sweep. FIG. 9C shows pie shaped incision region 572 with a having both a curved and linear perimeter. The shape of the incision region may further include one or more parallelograms, rectangles, pentagons, hexagons, conic sections such as parabolas and hyperbolas, circles, tear shapes, chord shapes and cross shapes.

The size and shape of the incising regions in the multiple sweeps can be optimally designed to produce fast and effective scanning patterns for performing incisions. An example of the manner and design of incising regions for performing efficient ophthalmic incisions shall be described for lenticular incisions.

Figure 10:
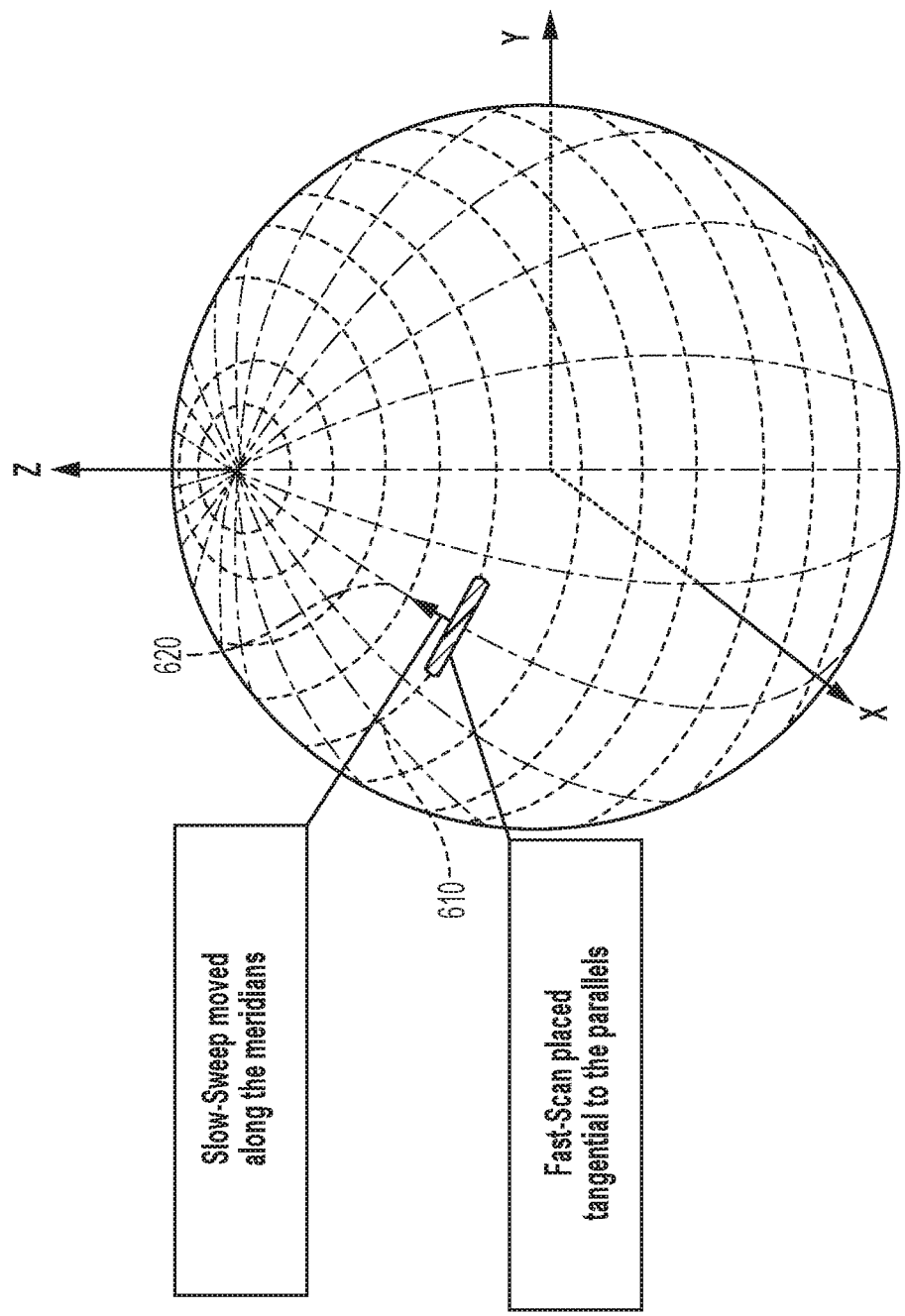
FIG. 10 illustrates an exemplary lenticular incision using a fast-scan-slow-sweep scheme of a surgical ophthalmic laser system according to an embodiment of the present invention.

In another embodiment shown in FIG. 10, the laser system 10 creates a smooth lenticular cut using the "fast-scan-slow-sweep" scanning scheme under a preferred procedure. First, in a three dimensional lenticular cut, the fast scan line is preferably placed tangential to the parallels of latitude 610. For example, in the miniaturized flap maker laser system 10 of FIG. 3, this can be realized by adjusting a prism 23 to the corresponding orientations via software, e.g., via the controller 22. Second, the slow sweep trajectory preferably moves along the meridians of longitude 620. For example, in the miniaturized flap maker system of FIG. 3, this can be done by coordinating the XY scanner 28, and the Fast-Z scanner 20 via the software, e.g., via the controller 22. The procedure starts with the scan line being parallel to the XY plane, and sweeps through the apex of the lens, following the curvature with the largest diameter (see also FIG. 12). With this preferred procedure, there are no vertical "steps" in the dissection, and vertical side cuts are eliminated. As will be analyzed herein below, the deviations between the laser focus locations and the intended spherical surface dissections are also minimized.

Figure 11:
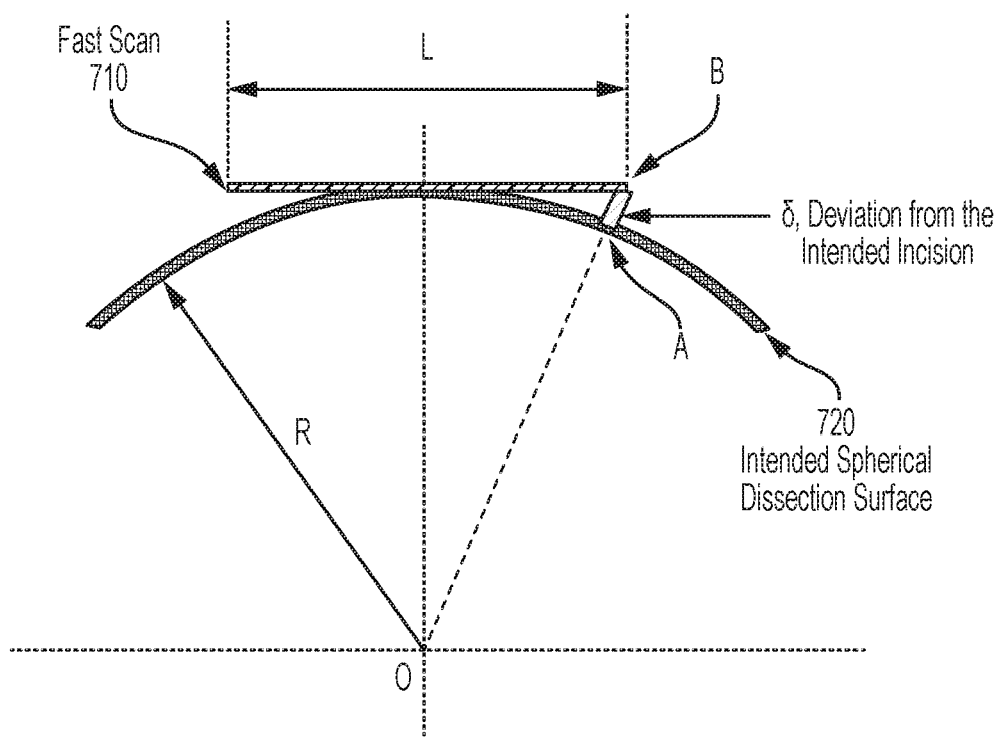
FIG. 11 illustrates a geometric relation between a fast scan line and an intended spherical dissection surface of a surgical ophthalmic laser system according to an embodiment of the present invention.

FIG. 11 shows the geometric relation between the fast scan line 710 and the intended spherical dissection surface 720, e.g., of a lens, especially the distance deviation (δ) between the end point B of the scan line 720 and point A on the intended dissection surface 720. The maximum deviation δ is the distance between point A and point B, and is given by $$\delta = \sqrt{R^2 + \frac{L^2}{4}} - R = \frac{L^2}{8R}, \quad \text{equation (1)},$$

where R is greater than L. R is the radius of curvature of the surface dissection 720, and L is the length of the fast scan.

In an exemplary case of myopic correction, the radius of curvature of the surface dissection may be determined by the amount of correction, ΔD, using the following equation $$\Delta D = \frac{(n-1)}{R_1} + \frac{(n-1)}{R_2}, \quad \text{equation (2)},$$

where n=1.376, which is the refractive index of cornea, and $R_1$ and $R_2$ (may also be referred herein as $R_t$ and $R_b$) are the radii of curvature for the top surface and bottom surface of a lenticular incision, respectively. For a lenticular incision with $R_1=R_2=R$ (the two dissection surface are equal for them to physically match and be in contact), we have $$R = \frac{2(n-1)}{\Delta D}, \quad \text{equation (3)}.$$

Figure 12:
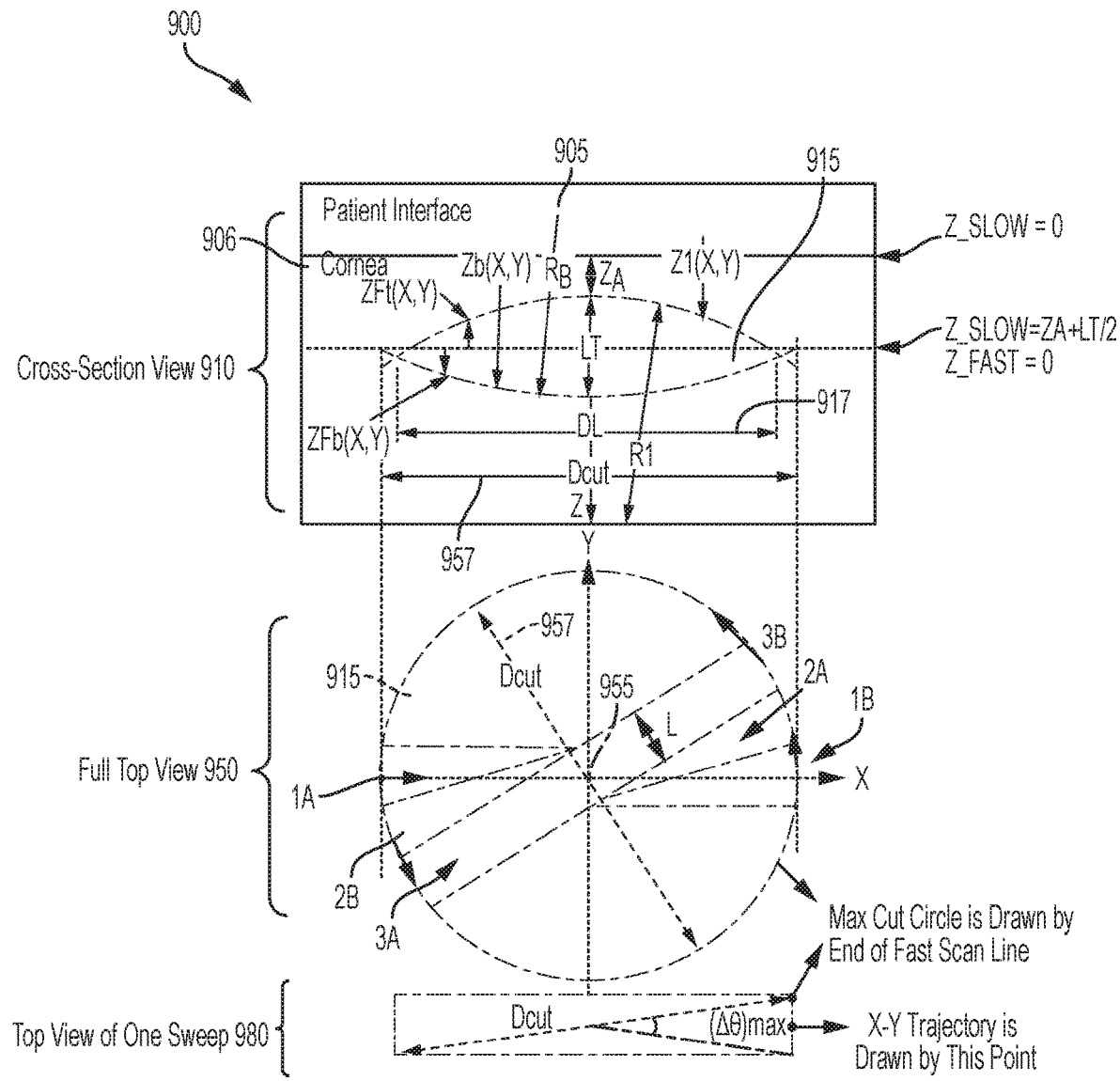
FIG. 12 illustrates an exemplary lenticular incision using a surgical ophthalmic laser system according to an embodiment of the present invention.

In an embodiment, FIG. 12 shows an exemplary lenticular incision 900 for extraction using the laser system 10. FIG. 12 shows an exemplary cross-sectional view 910 illustrating a patient interface 905 (or patient interface 31 as shown in FIG. 3), cornea 906, and lenticular incision volume 915, which will be referred herein as lens to be extracted. Rt and Rb are the radii of curvature for the top surface and bottom surface of a lenticular incision, respectively. ZFt (Zt) is the depth of the top surface of the lenticular incision. ZFb (Zb) is the depth of the bottom surface of the lenticular incision. The Z depths may be calculated based on the respective radii. LT is the lens thickness at the lens apex, or center thickness of the lens. ZA is depth of the lens apex. DL is the diameter of the lenticular incision, or the lens. {Z_SLOW=0} is the Z reference position before the laser system 10 calculates and sets Z_SLOW, e.g., {Z_SLOW=ZA+LT/2} the center depth of the lens, which remains fixed for the duration of the incision procedure. Z_SLOW may then be the reference position for the Z-scanner for top and bottom incision surfaces. In an embodiment, the diameter of the lens may be received from an operator of the laser system 10, or may be calculated by the laser system 10. The thickness of the lens may be determined, for example, by the total amount of correction (e.g., diopter) and the diameter of the lens.

A top view 950 of the lenticular incision 900 illustrates three exemplary sweeps (1A to 1B), (2A to 2B) and (3A to 3B), with each sweep going through (i.e., going over) the lenticular incision apex 955. The incision, or cut, diameter 957 ($D_{CUT}$) should be equal to or greater than the to-be-extracted lenticular incision diameter 917 (DL). A top view 980 shows the top view of one exemplary sweep. In an embodiment, the lenticular incision is performed in the following steps:

1. Calculate the radius of curvature based on the amount of correction, e.g., a myopic correction.

2. Select the diameter for the lenticular incision to be extracted.

3. Perform the side incision first (not shown) to provide a vent for gas that can be produced in the lenticular surface dissections. This is also the incision for the entry of forceps and for lens extraction.

4. Perform bottom surface dissection (the lower dissection as shown in cross-sectional view 910). In doing so, the fast scan line is preferably kept tangential to the parallels of latitude, and the trajectory of the slow sweep drawn by X, Y, and Z scanning devices moves along the meridians of longitude (near south pole in a sequence of 1A→1B (first sweep of lenticular cut), 2A→2B (second sweep of lenticular cut), 3A→3B (third sweep of lenticular cut), and so on, until the full bottom dissection surface is generated.

5. Perform the top surface dissection (the upper dissection as shown in the cross-sectional view 910) in a similar manner as the bottom dissection is done. It is noted that the bottom dissection is done first. Otherwise, the bubble generated during the top dissection will block the laser beam in making the bottom dissection.

For illustrative purposes, in a myopic correction of ΔD=10 diopter (i.e., 1/m), using equation (3), R=75.2 mm, which is indeed much greater than the length L of the fast scan. Assuming a reasonable scan line length of L=1 mm, using equation (1), the deviation δ=1.7 μm. This deviation is thus very small. For comparison purpose, the depth of focus of a one micron (FWHM) spot size at 1 μm wavelength is about ±3 μm, meaning the length of focus is greater than the deviation δ.

Figure 13:
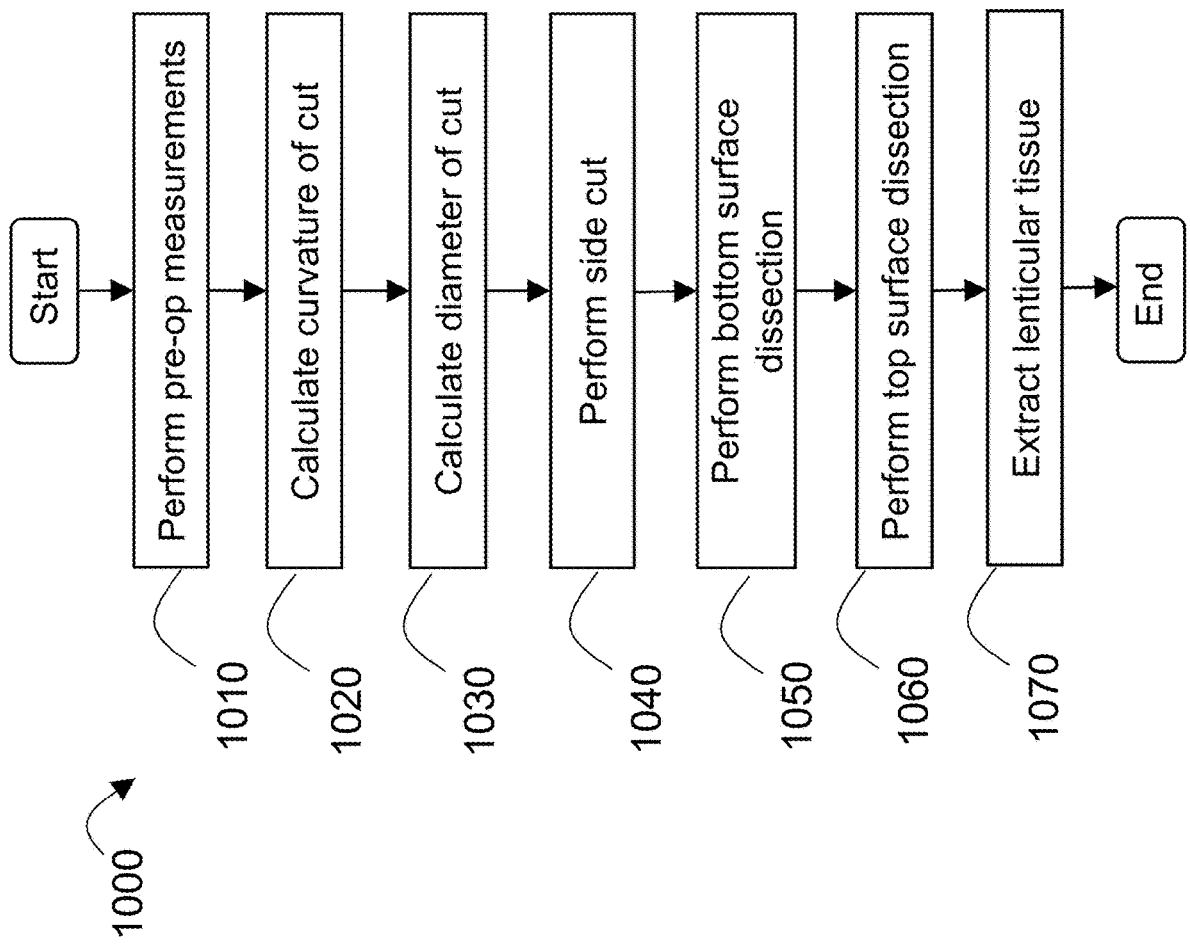
FIG. 13 is a flowchart illustrating a process according to an embodiment of the present invention.
Figure 14:
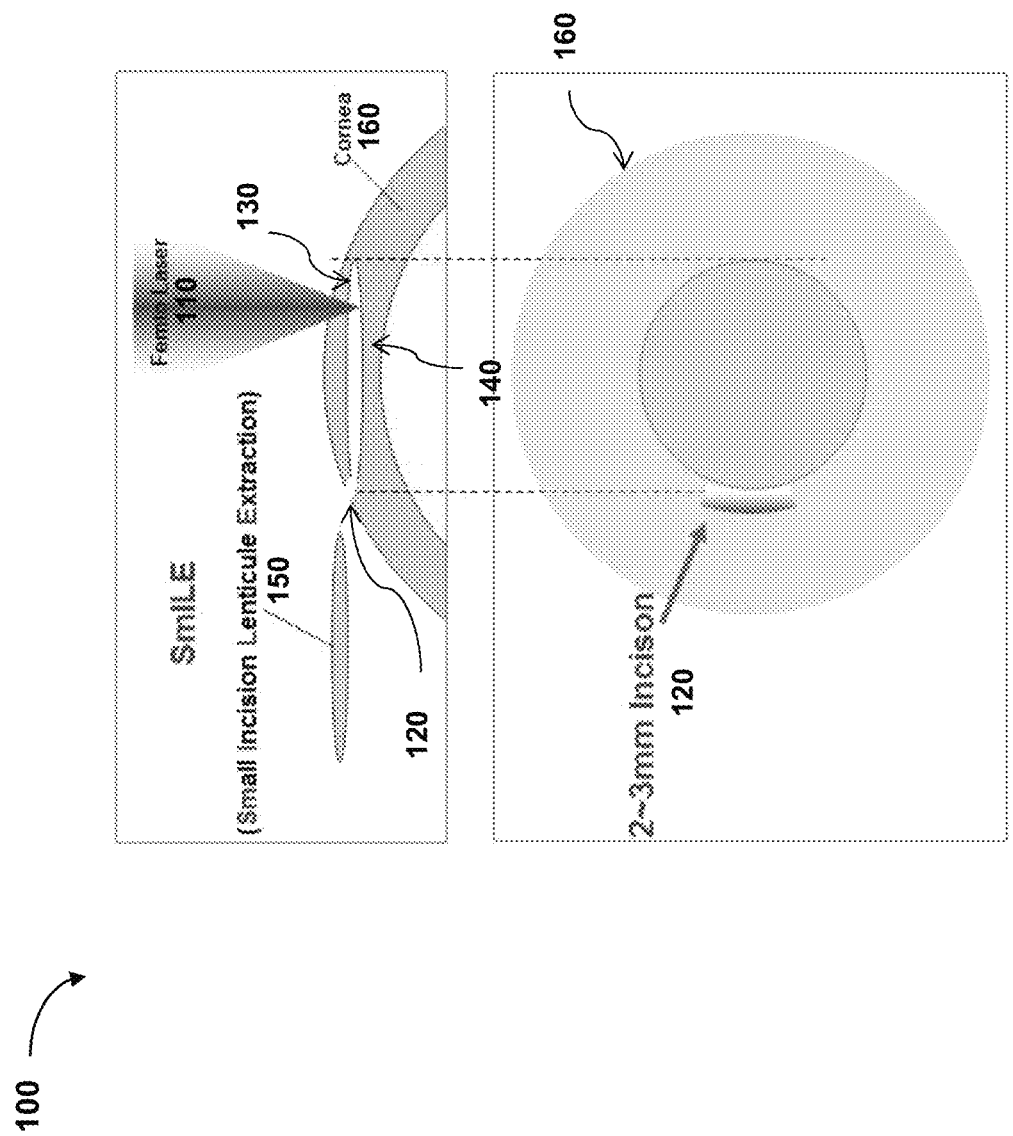
FIG. 14 illustrates a conventional Small Incision Lenticule Extraction procedure.

FIG. 13 illustrates a process 1000 of the laser system 10 according to an embodiment. The laser system 10 may start a surgical procedure performing pre-operation measurements (Action Block 1010). For example, in an ophthalmologic surgery for myopic correction, the myopic diopter is determined, the SLOW_Z position is determined, and so on. The laser system 10 calculates the radius of curvature based on the amount of correction, e.g., the myopic correction determined in pre-operation measurements (Action Block 1020), as shown, for example, in equations (2) and (3) above. The laser system 10 calculates the diameter of the incision (Action Block 1030), as shown by $D_{CUT}$ in FIG. 12.

$D_{CUT}$ is equal to or greater than the diameter of the to-be-extracted lenticule (DL in FIG. 12). The laser system 10 first performs side incision to provide a vent for gas that can be produced in the lenticular surface dissections, and for tissue extraction later on (Action Block 1040). The laser system 10 then performs the bottom lenticular surface dissection (Action Block 1050) before performing the top lenticular surface dissection (Action Block 1060). The lenticular tissue is then extracted (Action Block 1070).

In other embodiments, the laser system 10 may also be used to produce other three-dimensional surface shapes, including toric surfaces for correcting hyperopia and astigmatism. The laser system 10 may also be used for laser material processing and micromachining for other transparent materials. Correction of hyperopia by the laser system 10 is discussed in detail below.

Figure 15:
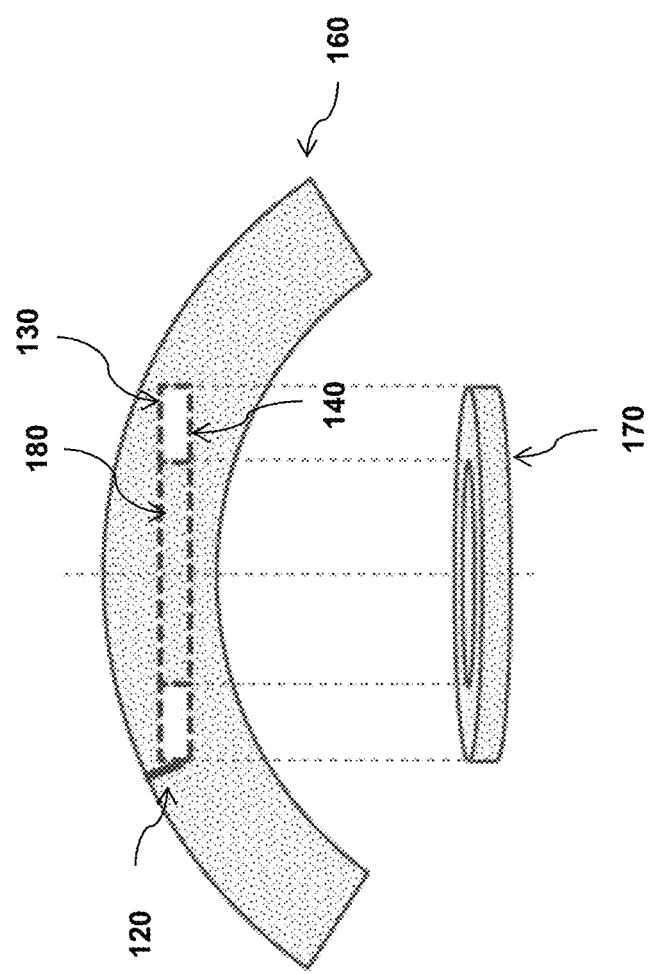
FIG. 15 illustrates a hypothetical Small Incision Lenticule Extraction procedure.

Conventional laser surgery methods to correct hyperopia utilize cut patterns including ring-shaped incision patterns that steepen the curvature of a cornea. However, FIG. 15 illustrates why utilizing these patterns using the known small incision lens extraction (SmILE) procedure is impractical and unfeasible. The cross-sectional view of the cornea 160 in FIG. 15 includes a sidecut 120, an upper surface cut 130, lower surface cut 140 and a ring-shaped cut 170 generated by a SmILE procedure. However, the cornea 160 maintains an uncut annular center portion 180 that remains attached to an anterior portion and posterior portion of the cornea 160.

This cut pattern is geometrically problematic as the clean removal of the ring cut 170 through the side cut 120 as a single ring is impeded by the center portion 180. Whereas a flap provided in a LASIK procedure allows a ring shape to be easily extracted, the use of a sidecut without a flap prevents the ring-shaped stroma material from being extracted from the tunnel like incision without breaking apart. Thus, a ring-shaped lenticule is not suitable for correcting hyperopia using the SmILE procedure since the ring cut 170 will break up unpredictably during removal through the side cut 120.

Some LASIK procedures correct hyperopia by removing cornea stroma material to increase the steepness of the cornea. For example, outward portions of the cornea are cut and removed while a center portion remains untouched except for the flap. Once the flap is folded back over, the flap fills the void vacated by the removed cornea stroma material and merges with the cornea. The cornea thus becomes steeper and a desired vision correction is achieved. However, the curve of the flap does not match the curve of the cornea such that the merger of the flap and cornea creates folds in the stroma that increase light scattering and create undesirable aberrations.

Figure 16:
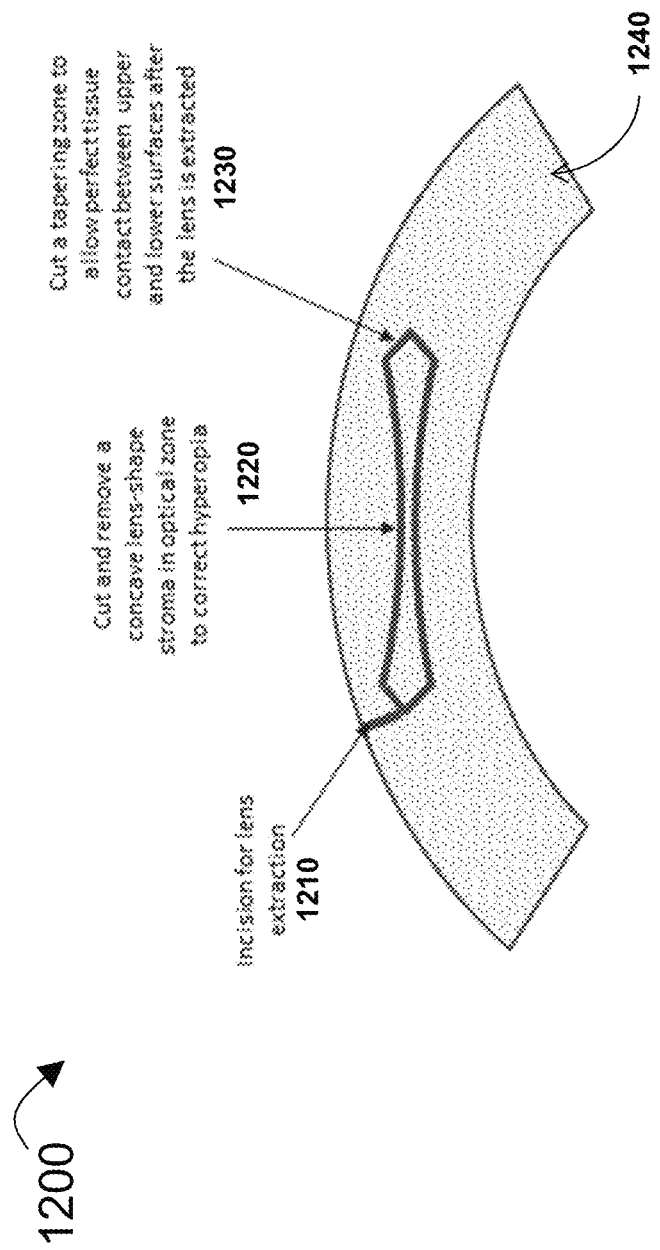
FIG. 16 illustrates an exemplary lenticular incision process according to an embodiment of the present invention.

FIG. 16 illustrates an exemplary lenticular incision 1200 that steepens the cornea by cutting and removing a symmetric concave lens-shaped stroma material from a cornea 1240. From an optical focus power perspective, the concave shape of the lenticule 1220 is equivalent to steepening the cornea or adding a convex lens in front of the eye.

Furthermore, extraction of the lenticule 1220 as a whole piece through a sidecut incision 1210 is assured and improved over a ring-shape cut, or a tunnel-like cut, or a toric cut. The incision includes a peripheral portion 1230 or tapering portion providing ideal merging of the cornea after the lenticule 1220 is extracted without folding in a top surface or bottom surface.

Figure 17:
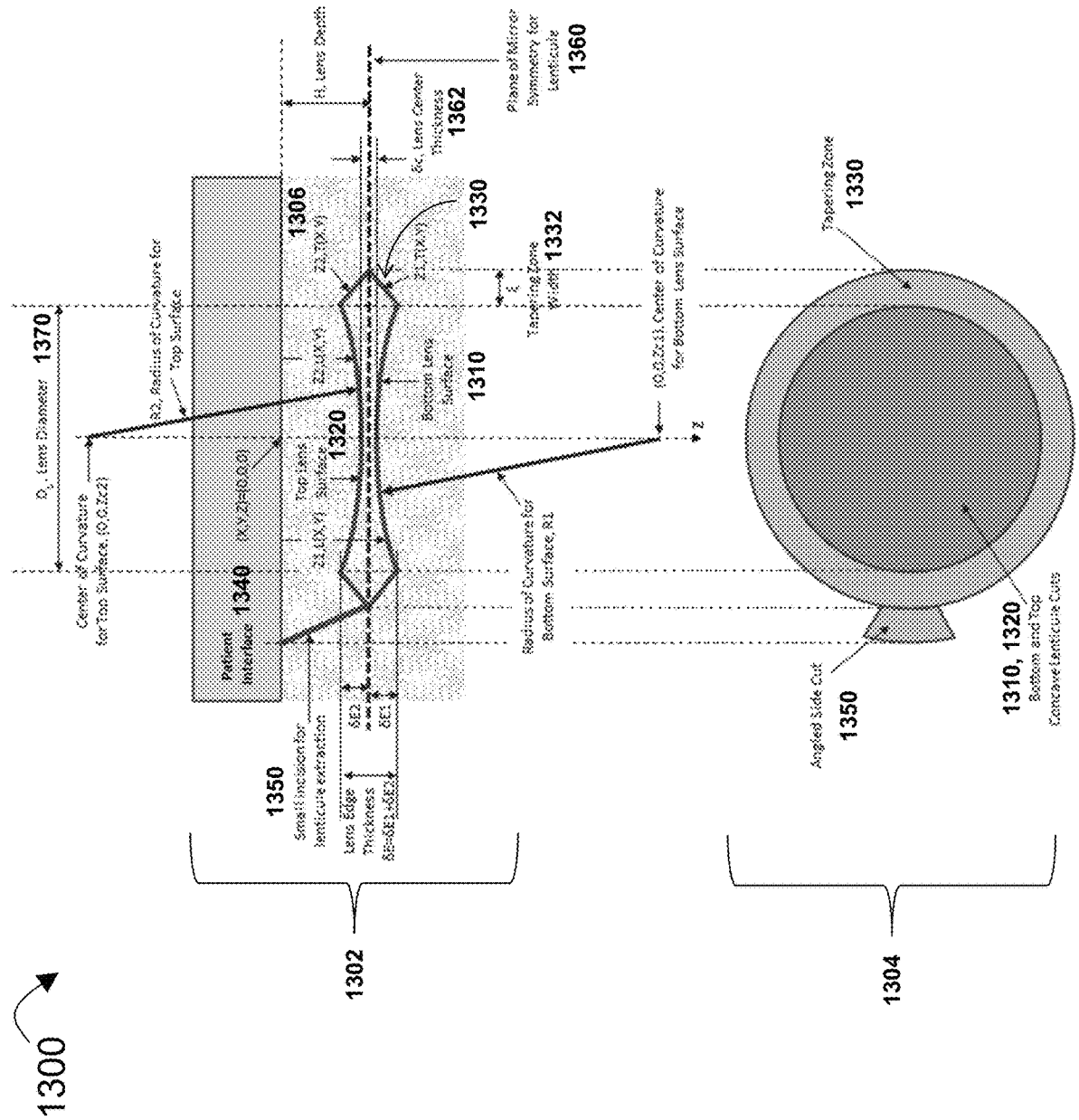
FIG. 17 illustrates an exemplary lenticular incision using a surgical ophthalmic laser system according to an embodiment of the present invention.

FIG. 17 illustrates an exemplary lenticular incision 1300 using a surgical ophthalmic laser system according to an embodiment of the present invention. For example, SmILE techniques may be applied in conjunction with FIG. 17 to treat hyperopia using a sub-nanosecond laser. A cross-sectional view 1302 and top view 1304 are provided of the lenticule cuts 1310, 1320 and side cut 1350. In FIG. 17, a patient interface 1340 is pressed against a cornea 1306. The lenticular incision includes a bottom lens surface 1310 and a top lens surface 1320. The bottom surface 1310 includes a radius of curvature R1 and the top surface 1320 includes a radius of curvature R2.

A side cut 1350 is performed first to provide a path for gas to vent to prevent the formation of bubbles. A bottom surface cut 1310 is then performed prior to performing a top surface cut 1320 to prevent the cutting beam from being blocked by bubbles generated by previous cornea dissection. The top and bottom surface cuts each include a central portion and a peripheral portion. The central portions are concave while the peripheral portions of the top and bottom cuts tapers (diminishes) towards each other to meet. The tapering peripheral portions minimize light scattering at the edges and further optimizes the matching of the cut surfaces and prevent folding after the lenticule has been removed.

As shown in FIG. 17, the thickest portion of the cut is provided at the boundary of the taper portion and the concave portion. For the top and bottom surfaces to match after lens extraction, the bottom and top surfaces are preferably mirror symmetric about a plane 1360.

These exemplary lenticular incisions allow lenticular tissue to be extracted in a single unbroken piece through the sidecut. The taper of the peripheral portions allows smooth extraction through the sidecut as a gradual slope is provided. The peripheral portions also support the merging of the top and bottom portions of the cornea as a top surface and bottom surface compress back together to form a smooth merge. Without a taper to the peripheral portions, the apex of the central portions would never merge and would form a permanent gap.

A concave lens cut includes a top concave lenticular incision and a bottom concave lenticular incision of a lens in the subject's eye. The concave lens cut may include at least one of a spherical surface, a cylindrical component, and any high order component. The top concave lenticular incision and the bottom concave lenticular incision may be mirror symmetric or nearly mirror symmetric to each other so long as the merging of the top surface and bottom surface does not create folding.

The system may operate with a laser having a wavelength in a range between 350 nanometers and 1100 nanometers and a pulse width in a range between 10 femtoseconds and 1 nanosecond.

In prior art solutions, a top layer cut is longer than a bottom layer cut. Under this configuration, the top and bottom cornea portions do not ideally merge as the top surface must fold in and compress in order to merge with shorter layer cut. With this fold created by the dissection, light scattering is increased. In contrast, a mirror symmetric cut along a center line allows ideal merge with no folding between a top layer and bottom layer. Consequently, there is less light scattering.

A lens edge thickness is given by $\delta_E$, $\delta_{E1}$, $\delta_{E2}$. A lens depth H is given as a distance between an anterior of the cornea 1306 and the plane 1360. The bottom surface 1310 and top surface 1320 have a lens diameter $D_L$, a lens center thickness $\delta c$ and a shape defined by respective curves $Z_{1,L}(x,y)$ and $Z_{2,L}(x,y)$. In order to minimize the amount of dissected cornea stroma material removed, the central thickness $\delta c$ should be minimized. For example, the central thickness may be a few μm, which can be achieved by using a laser beam with a high numerical aperture (such as NA=0.3–0.8, preferably NA=0.6).

Each of the bottom lens surface cut 1310 and the top lens surface cut 1320 includes a tapering zone 1330 along a periphery of the cuts. The tapering zone 1330 is defined by a tapering zone width and the curves $Z_{1,T}(x,y)$ and $Z_{2,T}(x,y)$.

A sidecut 1350 is provided from a surface of the cornea to the tapering zone 1330 for removal of the lenticule. The sidecut may meet the tapering zone 1330 on the mirror plane 1360 or other suitable extraction point.

With these parameters as described and illustrated, a set of equations are provided below that determine the three-dimensional shape of the lenticular cuts, assuming that the desired correction is purely defocus:

$$Z_{1,L}(x, y) = H + \frac{\delta_C}{2} + R_1 - \sqrt{R_1^2 - x^2 - y^2} \quad \text{Eq. (4)}$$
$$\text{for}$$
$$\sqrt{x^2 + y^2} \leq \frac{D_L}{2}$$

$$Z_{2,L}(x, y) = H - \frac{\delta_C}{2} - R_2 + \sqrt{R_2^2 - x^2 - y^2} \quad \text{Eq. (5)}$$
$$\text{for}$$
$$\sqrt{x^2 + y^2} \leq \frac{D_L}{2}$$

$$Z_{1,T}(x, y) = H + \delta_{E1} - \left(\sqrt{x^2 + y^2} - \frac{D_L}{2}\right) \cdot \frac{\delta_{E1}}{\xi} \quad \text{Eq. (6)}$$
$$\text{for}$$
$$\frac{D_L}{2} \leq \sqrt{x^2 + y^2} \leq \frac{D_L}{2} + \xi$$

$$Z_{2,T}(x, y) = H - \delta_{E2} + \left(\sqrt{x^2 + y^2} - \frac{D_L}{2}\right) \cdot \frac{\delta_{E2}}{\xi} \quad \text{Eq. (7)}$$
$$\text{for}$$
$$\frac{D_L}{2} \leq \sqrt{x^2 + y^2} \leq \frac{D_L}{2} + \xi$$

$$\delta_{E1} = \frac{\delta_C}{2} + R_1 - \sqrt{R_1^2 - \left(\frac{D_L}{2}\right)^2} \quad \text{Eq. (8)}$$

$$\delta_{E2} = \frac{\delta_C}{2} + R_1 - \sqrt{R_2^2 - \left(\frac{D_L}{2}\right)^2} \quad \text{Eq. (9)}$$

The shape and dimensions of the cuts may include additional correction for higher order aberrations and may be computed from measured vision errors. In some embodiments, approximately 50% of the total hyperopic correction is applied to each of the two mutually mirror-imaged cut surfaces.

It is noted that the thickest portion of the concave lens cut is provided at the intersection of the tapering zone and the concave lens cuts which correspond to a portion of the cornea that is thicker than a center portion of the cornea. Consequently, from the standpoint of cornea thickness, correcting hyperopia is more tolerable than correcting myopia, where the thicker portion of the lens to be removed is at the center of the cornea, corresponding to a thinner portion of the cornea.

The shape of the tapering zone 1330 need not be linear in shape. The tapering zone may be curved or any shape that minimizes light scattering at the cutting junctions and optimizes the matching of the two cut surfaces after lens extraction. The peripheral zone may be linear or a higher order polynomial.

Some embodiments of the invention apply to single-spot scanning methods applied in femtosecond laser systems. The invention also applies to cornea incisions using UV 355 nm sub-nanosecond lasers.

For illustrative purposes, Equations (2), (8) and (9) are used to estimate the thickness of the concave lens. In a hyperopic correction of $\Delta D=5$ diopter (which is high end values for LASIK hyperopia procedures) and assuming that a symmetric shape of the lenticule is selected, $R_1=R_2=150.4$ mm. Assuming $D_L=7.0$ mm and $\delta_C=10$ μm, then $\delta_E=\delta_{E1}+\delta_{E2}\approx\delta_C+D_L^2\cdot\Delta D/[8(n-1)]\approx 92$ μm.

Figure 18B:
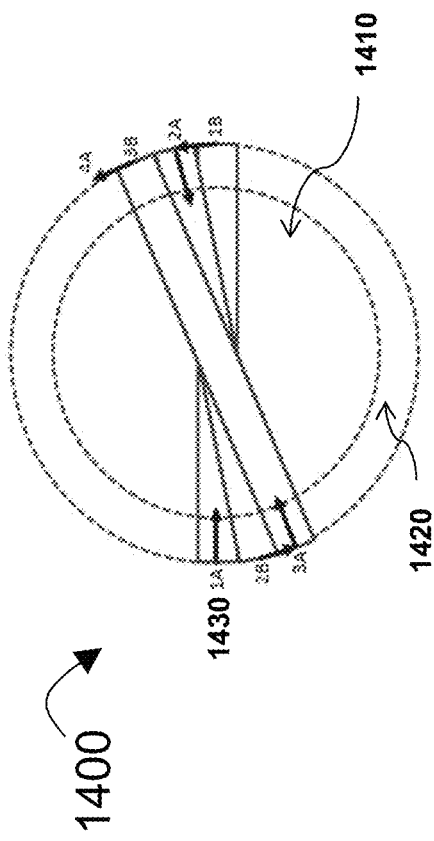
FIG. 18B illustrates a high energy ring exposure created by multiple overlapping sweeps of a surgical ophthalmic system in the prior art.
Figure 18A:
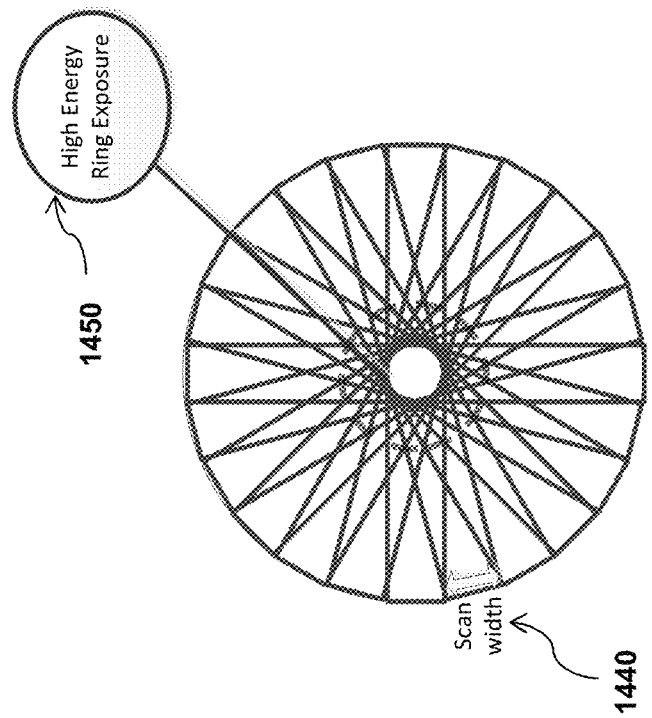
FIG. 18A illustrates an exemplary scanning process for performing a lenticular incision using the surgical ophthalmic laser system according to an embodiment of the present invention.

FIG. 18A illustrates an exemplary raster scanning process 1400 using a surgical ophthalmic laser system according to an embodiment of the present invention. FIG. 18A illustrates another embodiment of the "Fast-Scan-Slow-Sweep" scanning described previously. While performing an XY scan, Z values can be calculated from Eqs. (1)-(9), and the desired three-dimensional concave lens-shape cutting surfaces may be generated.

A top view of the lenticular incision illustrates three exemplary sweeps 1430 (1A to 1B), (2A to 2B) and (3A to 3B), with each sweep going through (i.e., going over) the concave lenticular incision 1410 and tapering zone 1420. In an embodiment, the lenticular incision is performed in the following steps:

1. Calculate the radius of curvature based on the amount of correction, e.g., a hyperopic correction.
2. Select the diameter for the lenticular incision to be extracted.
3. Calculate the shape of the lenticular incisions (concave surface and taper).
4. Perform the side incision first (not shown) to provide a vent for gas that can be produced in the lenticular surface dissections. This is also the incision for the entry of forceps and for lens extraction.
5. Perform bottom surface dissection (the bottom dissection 1310 as shown in cross-sectional view). In doing so, the fast scan line is preferably kept tangential to the parallels of latitude, and the trajectory of the slow sweep drawn by X, Y, and Z scanning devices moves along the meridians of longitude (near south pole in a sequence of 1A→1B (first sweep of lenticular cut), 2A→2B (second sweep of lenticular cut), 3A→3B (third sweep of lenticular cut), and so on (4A), until the full bottom dissection surface is generated.
6. Perform the top surface dissection 1320 in a similar manner as the bottom dissection is done. It is noted that the bottom dissection is done first. Otherwise, the bubble generated during the top dissection will block the laser beam in making the bottom dissection.

As shown in FIG. 18A the sweep sequence generated according to Steps 5 and 6 above result in a plurality of overlapping sweeps resulting in overlap regions of multiple sweeps used in performing the full bottom dissection and the top surface dissection. As shown in FIG. 18B, if the multiple sweeps were carried out with an invariant scan line, the sweep sequence 1A→1B (first sweep of lenticular cut), 2A→2B (second sweep of lenticular cut), 3A→3B (third sweep of lenticular cut), and so on (4A), the overlap regions produced by an invariant scan line would include overlap region 1450 that would comprise a ring of very high energy exposure which would be subject to numerous exposures if the pulse energy, repetition rate, and/or scan width of the scan line were not controlled according to the present invention. A ring of very high energy exposure would degrade the incision and potentially cause excess heat in the overlap region.

Figure 19A:
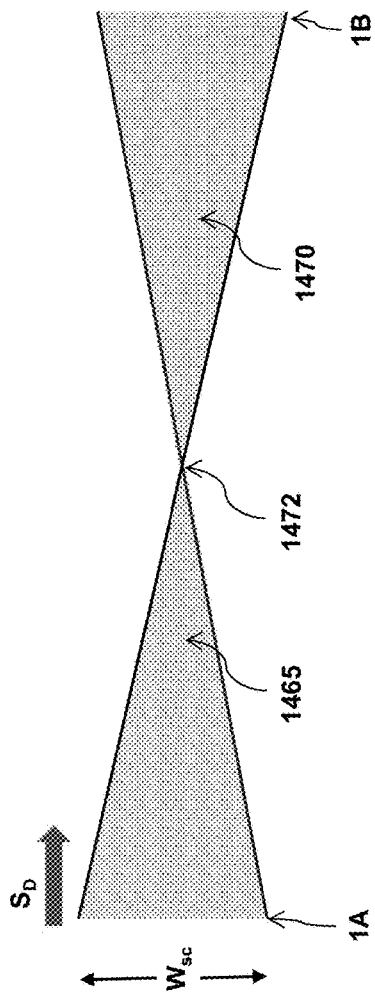
FIG. 19A illustrates an exemplary sweep sequence performed by the surgical ophthalmic laser system according to the present invention adapted for use in connection performing lenticular incisions according to an embodiment of the present invention.

A high energy ring exposure can be avoided by performing the sweeps of the scan line 501 where at least one of the energy of the laser pulses, the repetition rate and the scan width of scan line is controlled so as shown to perform sweeps 1A→1B (and subsequent sweeps) in a shape shown in FIG. 19A (substantially as shown and described in FIGS. 7A, 7B, and/or FIGS. 8A and 8B). As shown in FIG. 19A, the incised portions 1465, 1470 are both triangular and the triangles are connected at a vertex (crossing point 1472).

Figure 19B:
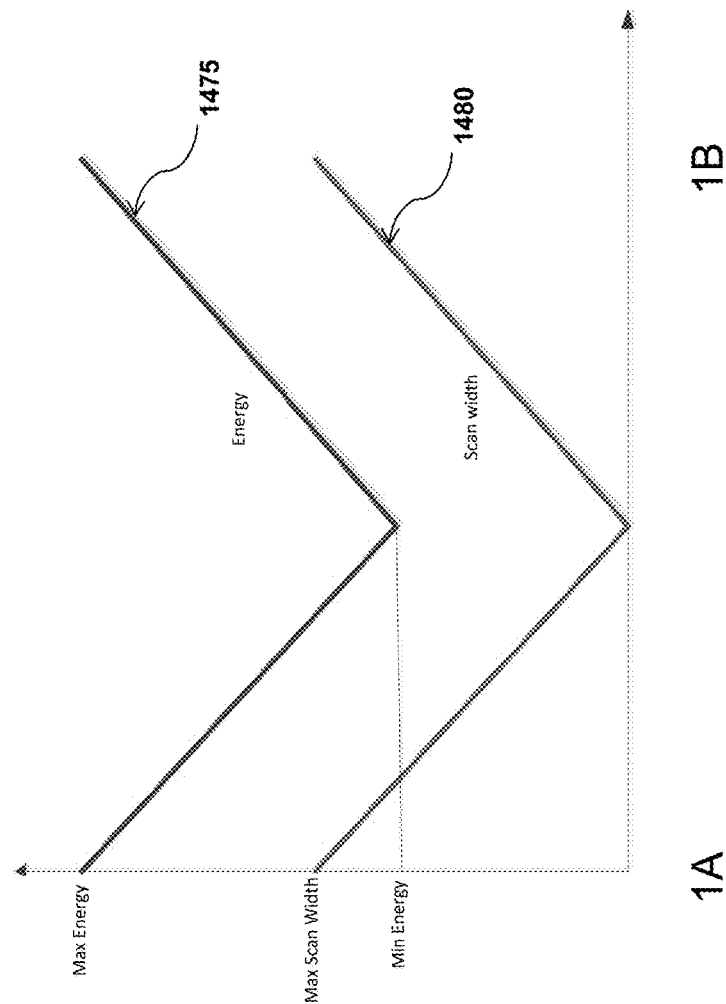
FIG. 19B is a graph of Energy (upper curve) and scan width (lower curve) as a function of position in the exemplary sweep shown in FIG. 19A.

In one embodiment of performing the sweep of FIG. 19A, an energy or repetition rate is controlled, and the size of the incising portion of the scan line (e.g. incising portion 525 in FIGS. 7A and 7B) is a maximum at the edges. The incising portion decreases continuously as the scan line is swept along the scan trajectory 1A→1B and reaches a minimum at a center 1472 over the surface of the spherical incision. After reaching the center 1472 over the surface of the spherical incision, the size of incising portion continuously increases as scan line 501 is swept to end point position 1B. Here, the incising portion of scan line 501 is comprised of laser pulses having a pulse energy and repetition rate sufficient to modify ophthalmic tissue. The non-incising portions of the scan line are characterized by a pulse energy and/or repetition rate below the level required to modify tissue. By controlling the incising portion in this manner, incised portion 1465, 170 are obtained. A graph of the energy of the scan line as a function of sweep position is shown in FIG. 19B (upper curve 1475).

In another embodiment of performing the sweep of FIG. 19A, a size of the scan line is controlled. The size of the scan width of the scan line 501 (e.g. 545 in FIGS. 8A and 8B) is a maximum at the edge of the scan and decreases continuously as the scan line is swept along the scan trajectory 1A→1B and reaches a minimum at a center 1472 over the surface of the spherical incision. After reaching the center 1472 over the surface of the spherical incision, the size of scan line continuously increases as scan line 501 is swept to end point position 1B. Here, the scan line 501 is comprised of laser pulses having a pulse energy and repetition rate sufficient to modify ophthalmic tissue. A graph of the scan width of the scan line as a function of sweep position is shown in FIG. 19B (lower curve 1480).

The following equations provide for the creation of the incising portions 1465, 1470 for the specific case of Myopic lenticular incision for the sweep sequence of FIG. 19A:

$$Z_{Fast}(X, Y) = \pm\left(\sqrt{R^2 - X^2 - Y^2} - R + \frac{L_T}{2}\right) \quad \text{(Equation 10)}$$

$$X_{ij} = \left(\frac{L_D}{2} - XYI_i\right)\text{Cos}(SLA - SCI_j) \quad \text{(Equation 11)}$$

$$Y_{ij} = \left(\frac{L_D}{2} - XYI_i\right)\text{Sin}(SLA - SCI_j) \quad \text{(Equation 12)}$$

$$ScanWidth_i = \left|ScanWidth - \frac{2ScanWidth}{XYI_i}\right| \quad \text{(Equation 13)}$$

$$Energy_i = \left|MaxEnergy - \frac{MaxEnergy}{E_i}\right|, \quad \text{(Equation 14)}$$

Figure 20:
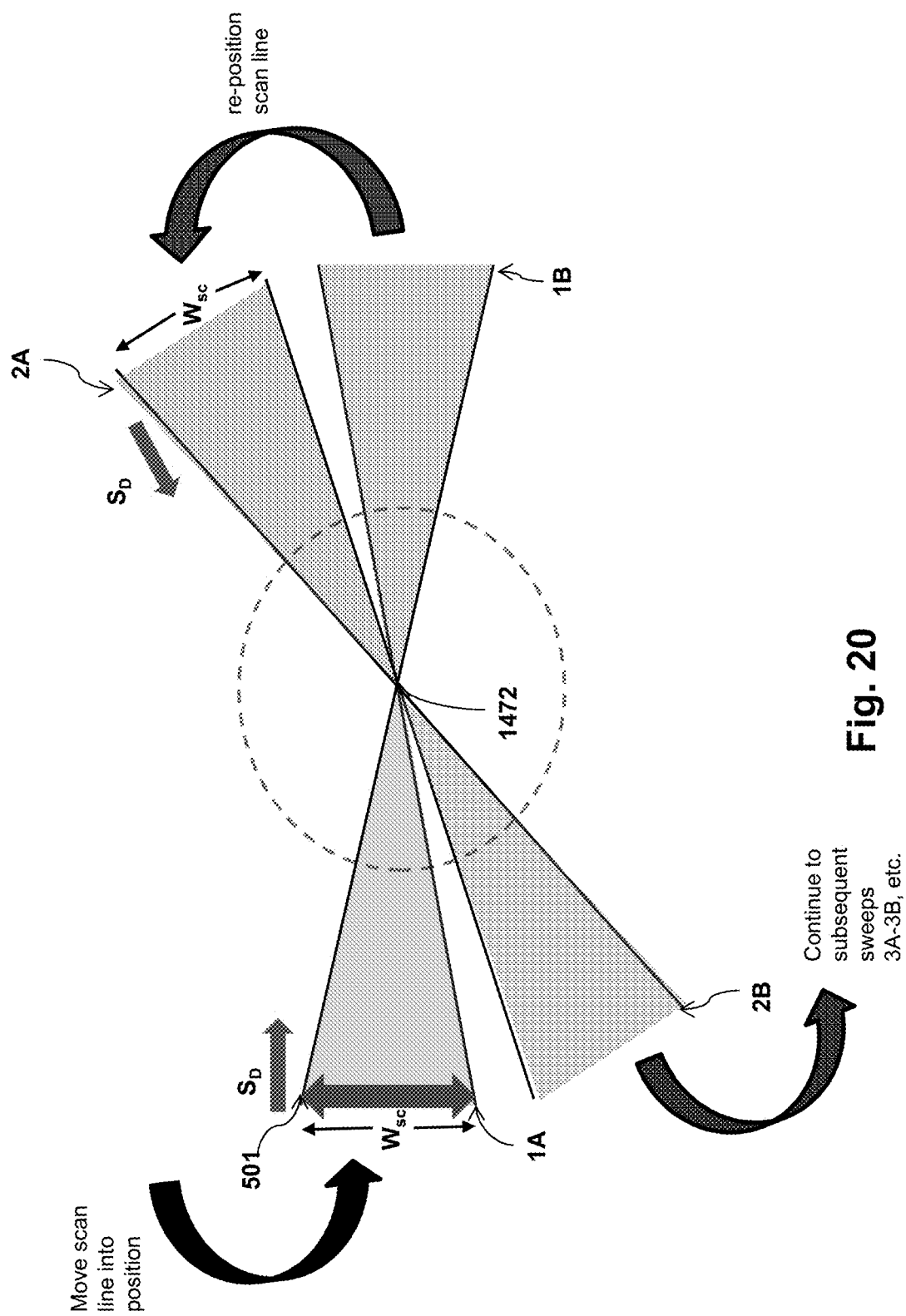
FIG. 20 illustrates an exemplary plurality of sweep sequences performed by the surgical ophthalmic laser system according to the present invention adapted for use in connection performing lenticular incisions according to an embodiment of the present invention.
Figure 21:
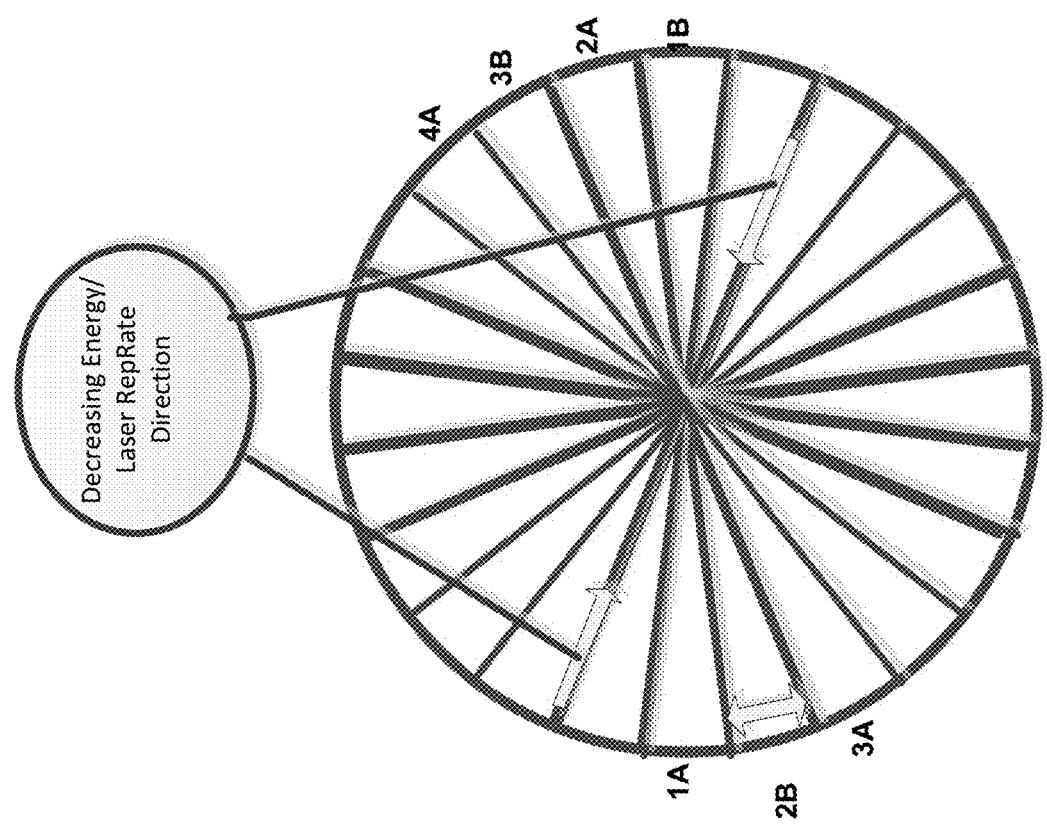
FIG. 21 illustrates a completed plurality of sweep sequences performed by the surgical ophthalmic laser system according to the present invention adapted for use in connection performing lenticular incisions according to an embodiment of the present invention.

Wherein,
$Z_{Fast}(X,Y)$ is the fast Z position over the lenticule surface
$L_D$ is the Lenticule diameter position
$XYI_i$ is the diameter increment
$SLA$ is the scan line angle
$SCI_j$ is the Scan line increment
$R$ is the radius of curvature of top or bottom surface
$E_i$ is the energy increment The sweep sequence 1A→1B (first sweep of lenticular cut) shown in FIG. 19A, can then be repeated sweep sequence 2A→2B (second sweep of lenticular cut), sweep sequence 3A→3B (third sweep of lenticular cut), and for each subsequent scan as shown in FIG. 20. Further, the plurality sweep sequence each have a common crossing point 1472. The plurality of sweep sequences performed in this manner result in a single crossing point 1472 and uniform energy distribution over the surface which would result in excellent surface uniformity and high quality lenticular incisions as shown in FIG. 21.

Figure 22:
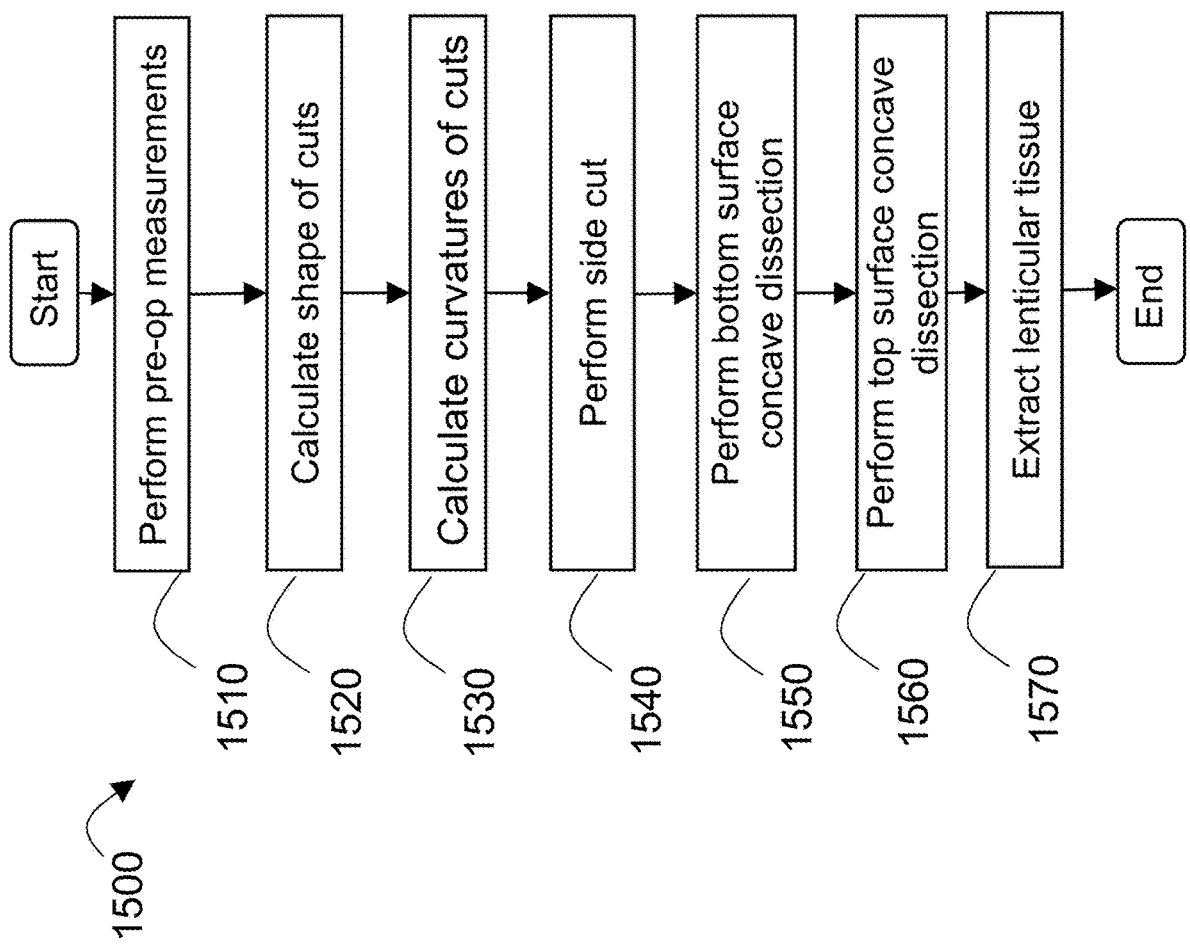
FIG. 22 is a flowchart illustrating an exemplary surgery process according to an embodiment of the present invention.

FIG. 22 is a flowchart illustrating an exemplary surgery process 1500 according to an embodiment of the present invention. The laser system 10 may start a surgical procedure performing pre-operation measurements (Action Block 1510). For example, in an ophthalmologic surgery for hyperopic correction, the hyperopic diopter is determined, the SLOW_Z position is determined, and so on. The laser system 10 calculates the shape of the incisions (Action Block 1520). The laser system 10 calculates the radius of curvatures based on the amount of correction, e.g., the hyperopic correction determined in pre-operation measurements (Action Block 1530), as determined by Equations (4)-(8), for example. The laser system 10 first performs a side incision to provide a vent for gas that can be produced in the lenticular surface dissections, and for tissue extraction later on (Action Block 1540). The laser system 10 then performs the bottom lenticular surface dissection (Action Block 1550) using the sweep sequence as shown in FIG. 19A before performing the top lenticular surface dissection using the sweep sequence shown in FIG. 19A (Action Block 1560). Performing the dissections in this order allows gas to vent out of the cornea instead of becoming trapped in gas bubbles within the cornea. The lenticular tissue is then extracted (Action Block 1570).

All patents and patent applications cited herein are hereby incorporated by reference in their entirety.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

What is claimed is:

1. An ophthalmic surgical laser system comprising:
   a laser delivery system for delivering a pulsed laser beam to a target in a subject's eye, the pulsed laser beam having a pulse energy and pulse repetition rate;
   a high frequency scanner configured to produce a scan line formed by the pulsed laser beam;
   an XY-scan device to deflect the scan line;
   a Z-scan device to modify a depth of a focus of the scan line; and
   a controller configured to:
   control the high frequency scanner to produce the scan line, the scan line having a scan width;
   control the XY-scan device and the Z-scan device to carry out of first sweep of the scan line in a first sweep direction;
   control the XY-scan device and the Z-scan device to carry out a second sweep of the scan line in a second sweep direction that is not parallel to the first sweep direction, thereby defining an overlap region, wherein at least one of the pulse energy, repetition rate, XY-scan speed, and the scan width are varied during at least one of the first sweep and second sweep so as to reduce an exposure of an ophthalmic tissue in the overlap region to multiple exposures of laser pulses configured to modify ophthalmic tissue.

2. The ophthalmic surgical laser system of claim 1, wherein the high frequency scanner is a resonant scanner.

3. The ophthalmic surgical laser system of claim 1 where the controller is further configured to control the XY-scan device and the Z-scan device to form a top lenticular incision and a bottom lenticular incision inside the cornea in the subject's eye.

4. The ophthalmic surgical laser system of claim 3, wherein the scan line is tangential to the parallels of latitude of the lenticule in the cornea.

5. The ophthalmic surgical laser system of claim 4, wherein the scan line is moved along the meridians of longitude of the lenticule in the cornea.

6. The ophthalmic surgical laser system of claim 5, wherein the top lenticular incision is moved over the top surface of the lenticule through the apex of the top surface of the lenticule, and the bottom lenticular incision is moved over the bottom surface of the lenticule through the apex of bottom surface of the lenticule.

7. The ophthalmic surgical laser system of claim 4, wherein there is a deviation between an end point of the scan line and a point on the spherical surface of the lenticule.

8. The ophthalmic surgical system of claim 1, wherein at least one of the pulse energy and repetition rate are varied such that an incising portion of the scan line varies during at least one of the first and second sweeps, thereby defining an incision region of the sweep.

9. The ophthalmic surgical system of claim 8, wherein a shape of the incision region includes one or more of triangles, trapezoids, parallelograms, rectangles, pentagons, hexagons, conic sections including parabolas and hyperbolas, circles, tear shapes, chord shapes and cross shapes.

10. The ophthalmic surgical system of claim 1, wherein the scan width varies during at least one of the first and second sweeps, thereby defining an incision region of the sweep.

11. The ophthalmic surgical system of claim 10, wherein a shape of the incision region includes one or more of triangles, trapezoids, parallelograms, rectangles, pentagons, hexagons, conic sections such as parabolas and hyperbolas, circles, tear shapes, chord shapes and cross shapes.

* * * * *